US012226421B2

(12) United States Patent
Fatholahi

(10) Patent No.: US 12,226,421 B2
(45) Date of Patent: *Feb. 18, 2025

(54) NEFOPAM DOSAGE FORMS AND METHODS OF TREATMENT

(71) Applicant: Shahin Fatholahi, Malvern, PA (US)

(72) Inventor: Shahin Fatholahi, Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,581

(22) Filed: Jul. 19, 2023

(65) Prior Publication Data

US 2023/0364108 A1 Nov. 16, 2023

Related U.S. Application Data

(63) Continuation of application No. 17/322,098, filed on May 17, 2021, now abandoned, which is a continuation of application No. 16/912,324, filed on Jun. 25, 2020, now Pat. No. 11,013,747, which is a continuation of application No. 15/699,856, filed on Sep. 8, 2017, now Pat. No. 10,736,905.

(60) Provisional application No. 62/464,218, filed on Feb. 27, 2017, provisional application No. 62/463,355, filed on Feb. 24, 2017, provisional application No. 62/385,675, filed on Sep. 9, 2016.

(51) Int. Cl.
A61K 31/485 (2006.01)
A61K 9/20 (2006.01)
A61K 31/19 (2006.01)
A61K 31/194 (2006.01)
A61K 31/395 (2006.01)
A61K 47/26 (2006.01)
A61K 47/32 (2006.01)
C07D 267/22 (2006.01)

(52) U.S. Cl.
CPC ........ *A61K 31/5545* (2017.08); *A61K 31/194* (2013.01); *A61K 47/26* (2013.01); *A61K 47/32* (2013.01); *C07D 267/22* (2013.01)

(58) Field of Classification Search
CPC .... A61K 31/485; A61K 31/19; A61K 9/0053; A61K 9/20
USPC ............. 514/211.09, 282, 568; 424/435, 464
See application file for complete search history.

(56) References Cited

U.S. PATENT DOCUMENTS

| | | |
|---|---|---|
| 2,798,053 A | 7/1957 | Brown |
| 2,909,462 A | 10/1959 | Warfield et al. |
| 3,133,132 A | 5/1964 | Sidney et al. |
| 3,173,876 A | 3/1965 | Zobrist |
| 3,276,586 A | 10/1966 | Rosaen |
| 3,541,005 A | 11/1970 | Baker et al. |
| 3,541,006 A | 11/1970 | Bixler et al. |
| 3,546,876 A | 12/1970 | Herman et al. |
| 3,830,803 A | 8/1974 | Draper et al. |
| 3,845,770 A | 11/1974 | Theeuwes et al. |
| 3,916,899 A | 11/1975 | Theeuwes et al. |
| 4,160,020 A | 7/1979 | Ayer et al. |
| 4,207,893 A | 6/1980 | Michaels |
| 4,327,725 A | 5/1982 | Cortese et al. |
| 4,855,294 A | 8/1989 | Patel et al. |
| 4,915,949 A | 4/1990 | Wong et al. |
| 5,002,776 A | 3/1991 | Geoghegan et al. |
| 5,051,260 A | 9/1991 | Chess et al. |
| 5,286,497 A | 2/1994 | Hendrickson et al. |
| 5,429,816 A | 7/1995 | Hofrichter et al. |
| 5,529,791 A | 6/1996 | Deboeck et al. |
| 5,552,136 A | 9/1996 | Motley |
| 5,643,588 A | 7/1997 | Roe et al. |
| 5,719,197 A | 2/1998 | Kanios et al. |
| 5,830,503 A | 11/1998 | Chen |
| 5,834,023 A | 11/1998 | Chen |
| 5,837,379 A | 11/1998 | Chen et al. |
| 5,965,163 A | 10/1999 | Miller et al. |
| 6,025,376 A | 2/2000 | Laurent et al. |
| 6,162,467 A | 12/2000 | Miller et al. |
| 6,270,805 B1 | 8/2001 | Chen et al. |
| 6,419,954 B1 | 7/2002 | Chu et al. |
| 6,524,620 B2 | 2/2003 | Chen et al. |
| 6,613,866 B2 | 9/2003 | Zofchak et al. |
| 6,638,528 B1 | 10/2003 | Kanios |
| 6,638,538 B1 | 10/2003 | Hashimoto et al. |
| 6,806,294 B2 | 10/2004 | Wimmer et al. |
| 6,923,984 B1 | 8/2005 | Remon |
| 6,946,120 B2 | 9/2005 | So et al. |
| 6,964,978 B2 | 11/2005 | Hageman et al. |
| 6,983,749 B2 | 1/2006 | Kumar et al. |
| 7,122,198 B1 | 10/2006 | Singh et al. |
| 7,399,488 B2 | 7/2008 | Hirsh et al. |

(Continued)

FOREIGN PATENT DOCUMENTS

| | | |
|---|---|---|
| EP | 0859766 | 5/2001 |
| EP | 1692118 | 4/2007 |

(Continued)

OTHER PUBLICATIONS

Kapfer et al., "Nefopam and Ketamine Comparably Enhance Post-Operative Analgesia," Anesth Analg. 100(1): 169-174 (2005).
Lasseter et al., "Nefopam HCl Interaction Study with Eight Other Drugs," J Int Med Res 4:195-201 (1976).
Girard et al., "Nefopam Analgesia and its Role in Multimodal Analgesia: A Review of Preclinical and Clinical Studies," Clinical and Experimental Pharmacology and Physiology 43( 1): 3-12 (2016).
Ahmad et al., "Study of Pharmacokinetics and Comparative Bioavailability of Nefopam 30 mg Tablets in Twelve Fasting Healthy Pakistani Male Young Subjects: Single-Dose Randomized, Two-Period, Two-Treatment and Two-Way Cross-Over Design," Med. Princ. Pract. 21: 271-276 (2012).

(Continued)

*Primary Examiner* — Raymond J Henley, III
(74) *Attorney, Agent, or Firm* — FLOREK & ENDRES PLLC

(57) ABSTRACT

Dosage forms containing nefopam, nefopam metabolite, nefopam prodrug, isomers thereof or combinations of the foregoing, optionally an acid, and optionally an opioid analgesic and/or NSAID, and associated methods for treating various types of pain in patients.

8 Claims, No Drawings

(56) References Cited

U.S. PATENT DOCUMENTS

| | | | |
|---|---|---|---|
| 7,449,613 B2 | 11/2008 | Klofta et al. | |
| 7,771,707 B2 | 8/2010 | Hirsh et al. | |
| 7,776,345 B2 | 8/2010 | Dudhara et al. | |
| 7,951,398 B2 | 5/2011 | Dietrich et al. | |
| 8,012,496 B2 | 9/2011 | Dudhara et al. | |
| 8,182,835 B2 | 5/2012 | Kim et al. | |
| 8,377,474 B2 | 2/2013 | Hsu et al. | |
| 8,383,152 B2 | 2/2013 | Jans et al. | |
| 8,440,170 B2 | 5/2013 | Stroppolo et al. | |
| 8,461,171 B2 | 6/2013 | Holaday et al. | |
| 8,513,304 B2 | 8/2013 | Kisak et al. | |
| 8,575,211 B2 | 11/2013 | Girard et al. | |
| 8,598,221 B2 | 12/2013 | Girard et al. | |
| 8,834,921 B2 | 9/2014 | Kim et al. | |
| 8,957,107 B2 | 2/2015 | Alman et al. | |
| 9,044,398 B2 | 6/2015 | Hirsh et al. | |
| 9,155,712 B2 | 10/2015 | Kanios et al. | |
| 9,168,228 B2 | 10/2015 | Tygesen et al. | |
| 9,205,052 B2 | 12/2015 | Kim et al. | |
| 9,566,263 B2 | 2/2017 | Alman et al. | |
| 10,736,905 B1* | 8/2020 | Fatholahi | C07D 267/22 |
| 2002/0165248 A1 | 11/2002 | Wimmer et al. | |
| 2004/0081682 A1 | 4/2004 | Guenther et al. | |
| 2006/0040905 A1 | 2/2006 | Lyne | |
| 2006/0063753 A1 | 3/2006 | Bannister et al. | |
| 2006/0160789 A1 | 7/2006 | Tirault et al. | |
| 2007/0042969 A1 | 2/2007 | Rauschkolb-Loffler et al. | |
| 2007/0043112 A1 | 2/2007 | Brew et al. | |
| 2007/0043120 A1 | 2/2007 | Beyreuther et al. | |
| 2007/0269379 A1 | 11/2007 | Mitragotri et al. | |
| 2007/0276137 A1 | 11/2007 | James | |
| 2008/0031942 A1 | 2/2008 | Uchiyama et al. | |
| 2008/0255079 A1 | 10/2008 | Lyne et al. | |
| 2009/0215844 A1 | 8/2009 | Davis et al. | |
| 2009/0227646 A1 | 9/2009 | Davis et al. | |
| 2009/0263476 A1 | 10/2009 | Jobdevairakkam et al. | |
| 2010/0152152 A1 | 6/2010 | Yne et al. | |
| 2010/0197777 A1 | 8/2010 | Girard et al. | |
| 2011/0275626 A1 | 11/2011 | Perovitch et al. | |
| 2011/0287094 A1 | 11/2011 | Penhasi et al. | |
| 2014/0356428 A1 | 12/2014 | Barnscheid et al. | |
| 2016/0310428 A1 | 10/2016 | Wening et al. | |

FOREIGN PATENT DOCUMENTS

| | | |
|---|---|---|
| WO | 1997015561 | 5/1997 |
| WO | 2003105833 | 12/2003 |
| WO | 2005060957 | 7/2005 |
| WO | 2009053742 | 4/2009 |
| WO | 2014186581 | 11/2014 |

OTHER PUBLICATIONS

Wang et al., "Pharmacokinetics and Bioequivalence of Sustained-Release Tablet of Nefopam," Chinese Journal of Clinical Pharmacology and Therapeutics (2002).

Feng, S. "The Preparation of Nefopam Hydrochloride Sustained-Release Tablets and Its Drug Release in Vitro," Journal of Beijing Union University (Natural Sciences) (2006).

Wu et al., "Preparation of Nefopam Hydrochloride Controlled Porosity Osmotic Pump by Central Composite Design," Journal of Shenyang Pharmaceutical University (2009).

Singh et al., "Formulation, Optimization and Evaluation of Sustained Release Microspheres Using Taguchi Design," Journal of Pharmaceutical Technology, Research and Management, 2(1): 1-12 (2014).

Chu et al., "Characterization of Transdermal Delivery of Nefopam Hydrochloride Under Iontophoresis," Drug Development and Industrial Pharmacy, 20(18): 2775-2785 (1994).

Wilkinson et al., "A Double-Blind Comparison of Nefopam and Placebo Used as a Premedication in Children," Anaesthesia 39: 815-819 (1984).

Manoir et al., "Randomized Prospective Study of Analgesic Effect of Nefopam After Orthopaedic Surgery," British Journal of Anesthesia 91(6): 836-841 (2003).

Nam et al., "Effects of Nefopam on Streptozotocin-Induced Diabetic Neuropathic Pain in Rats," Korean J. Pain 27(4): 326-333 (2014).

Impax Laboratories, Inc., "Safety and Efficacy Study of IPX159 in Restless Legs Syndrome (RLS)", Retrieved from https://clinicaltrials.gov/ct2/show/NCT01521663?term=IPX 159&rank=1, (2013).

Chawla et al., "Effect of Route of Administration on the Pharmacokinetic Behavior of Enantiomers of Nefopam and Desmethynefopam," Therapeutic Drug Monitoring 25:203-210 (2003).

Reich et al., "Chapter 18: Tonicity, Osmoticity, Osmolality and Osmolarity," Remington: The Science and Practice of Pharmacy, 20th Ed., Lippincott Williams and Wilkins, Philadelphia, PA. pp. 246-262 (2000).

Remington, Science and Practice of Pharmacy 21st Edition, pp. 1000-1017 (2005).

United States Pharmacopeia 29 (2006) pp. 3257-3261.

Martindale, "Nefopam Hydrochloride," The Compete Drug Reference, 33rd ed. Pharmaceutical Press, (edited by S.C. Sweetman et al.) p. 62 (2002).

The Merck Index, "Nefopam," 13th ed. Merck Research Laboratories, (edited by M.J. O'Neil et al.), entry 6469 (2001).

British Pharmacopoeia, "Nefopam Hydrochloride, Analgesics Antiinflammatory Drugs, and Antipyretics," 31 ed. p. 94 (2008).

Kim et al. "The Analgesic Efficacy and Safety of Nefopam in Patient-Controlled Analgesia after Cardiac Surgery: A Randomized, Double-Blind, Prospective Study," Journal of International Medical Research 42(3): 684-692 (2014).

Lee et al., "Nefopam vs Fentanyl in Female Patients Undergoing Laparoscopic Cholecystectomy," Enliven: J Anesthesiology and Critical Care Med. 1(3): May 26, 2014.

Yoon et al., "Post-Operative Intravenous Patient-Controlled Analgesic Efficacy of Morphine with Ketorolac Versus Nefopam after Laparoscopic Gynecologic Surgery: a Randomized Non-Inferiority Trial," Korean Journal of Anesthesiology (2016), 69 (2): 161-166.

Martinez et al., "Non-Opioid Analgesics in Adults after Major Surgery: Systematic Review with Network Meta-Analysis of Randomized Trials," British Journal of Anaesthesia (2017), 118 (1): 22-31.

Jin et al., "Opiod Sparing Effect and Safety of Nefopam in Patient Controlled Analgesia After Laparotomy: A Randomized, Double Blind Study," Journal of International Medical Research 44(3) 844-854, Apr. 2016.

Kapfer et al., "Nefopam and Ketamine Comparably Enhance Postoperative Analgesia." Anesth. Analg. 100(1): 169-174, Jan. 2005.

Moffat et al., "Postoperative Nefopam and Diclofenac: Evaluation of Their Morphine-Sparing Effect after Upper Abdominal Surgery," Anaesthesia, 1990, 45: 302-305.

Moon et al., "The Effect of Nefopam on Posteroperative Fentanyl Consumption: A Randomized, Double-blind Study," Korean Journal of Pain 29(2): 110-118, Apr. 2016.

Trop et al., "Comparison of Nefopam Hydrochloride and Propoxyphene Hydrochloride in the Treatment of Posteroperative Pain," Can. Anaesth. Soc. J., 26(4):296-304 Jul. 1979.

Laboureyras et al., "Long-Term Pain Vulnerability After Surgery in Rats: Prevention by Nefopam, an Analgesic with Antihyperalgesic Properties," Anesth. Analg., 109(2):623-31, Aug. 2009.

Buritova et. al., "Effects of Nefopam on the Spinal Nociceptive Processes: a c-Fos Protein Study in the Rat," European Journal of Pharmacology 441:67-74 (2002).

Brandow et al., "Neuropathic Pain in Patients with Sickle Cell Disease," Pediatric Blood Cancer, 61, pp. 512-517, Oct. 26, 2013.

Cho et al., "Antinociceptive Effect of Intrathecal Nefopam and Interaction with Morphine in Formalin-Induced Pain of Rats," Korean Journal of Pain 26:14-20 (2013).

Djerada et al., "Population Pharmacokinetics of Nefopam in Elderly, With or Without Renal Impairment, and its Link to Treatment Response," British Journal of Clinical Pharmacology 77:1027-1038 (2013).

(56) References Cited

OTHER PUBLICATIONS

Mimoz et al., "Nefopam Pharmacokinetics in Patients with End-Stage Renal Disease," Anesthesia and Analgesia 111:1146-1153 (2010).
Sanga et al. "Pharmacokinetics, Metabolism and Excretion of Nefopam, a Dual Reuptake Inhibitor in Healthy Male Volunteers," Xenobiotica 46:1001-1016 (2016).
Yu et al., "Pharmacokinetics, Distribution, Metabolism, and Excretion of the Dual Reuptake Inhibitor [14C]-Nefopam in Rats," Xenobiotica 46:1026-1048 (2016).
Zhang et al., "Comparison of the Effects of Nefopam and Tramadol on Postoperative Analgesia in Dogs Undergoing Ovariohysterectomy," Veterinarni Medicina, 62, pp. 131-137 (2017).
Ahmad et al., "Study of Pharmacokinetics and Comparative Bioavailability of Nefopam 30 mg Tablets in Twelve Fasting Healthy Pakistani Male Young Subjects: Single-Dose, Randomized, Two-Period, Two-Treatment and Two-Way Cross-Over Design," Medical Principles and Practice, 21, pp. 271-276 (2012).
Cohen et al., "Nefopam Hydrochloride: New Analgesic Agent," J. Int. Med. Res., 4, pp. 138-143 (1976).
Bassett et al., "Studies on the Peripheral Pharmacology of Fenazoxine, a Potential Antidepressant Drug," Br. J. Pharmac., 37, pp. 69-78 (1969).
Bhatt et al., "Respiratory and Metabolic Effects of Oral Nefopam in Human Volunteers" Br. J. Pharmac., 11, pp. 209-211 (1981).
Aymard et al., "Comparative Pharmacokinetics and Pharmacodynamics of Intravenous and Oral Nefopam in Healthy Volunteers", Pharmacology and Toxicology 92: 279-286 (2003).
Eremenko, et al., "Combination of Nefopam and Ketoprofen for Analgesia can Minimize Opioids Use in the Early Period after Cardiovascular Surgery: 14AP8-6", European Journal of Anaesthesiology 31: 236 (2014).
Mimoz et al., "Analgesic Eficacy and Safety of Nefopam vs. Propacetamol Following Hepatic Resection", Anaesthesia 56: 520-525 (2001).
Kim et al., "Rediscovery of Nefopam for the Treatment of Neuropathic Pain," Korean Journal of Pain, vol. 27, No. 2, pp. 103-111, Apr. 2014.

* cited by examiner

NEFOPAM DOSAGE FORMS AND METHODS OF TREATMENT

REFERENCE TO RELATED APPLICATIONS

This application is a continuation of U.S. patent application Ser. No. 17/322,098, filed May 17, 2021, which is a continuation of U.S. patent application Ser. No. 16/912,324, filed Jun. 25, 2020, now U.S. Pat. No. 11,013,747, which is a continuation of U.S. patent application Ser. No. 15/699,856, filed on Sep. 8, 2017, now U.S. Pat. No. 10,736,905, which claims the benefits of U.S. Provisional Patent Application Ser. No. 62/464,218 filed on Feb. 27, 2017; U.S. Provisional Patent Application Ser. No. 62/463,355 filed on Feb. 24, 2017; and U.S. Provisional Patent Application Ser. No. 62/385,675 filed on Sep. 9, 2016, the contents of all of which are hereby incorporated by reference in their entireties into the present application.

FIELD OF THE INVENTION

The present invention relates to new dosage forms of nefopam, nefopam metabolites, nefopam prodrugs and isolated isomers thereof and new uses of nefopam, nefopam metabolites, nefopam prodrugs and isolated isomers thereof in the treatment of certain types of pain.

BACKGROUND OF THE INVENTION

Nefopam is a centrally-acting non-opioid analgesic drug of the benzoxazocine chemical class. Nefopam has been known since the 1960s and its synthesis is described in U.S. Pat. No. 3,830,803. Nefopam is currently available around the world, but has not been approved by the U.S. Food and Drug Administration.

N-desmethyl nefopam is one metabolite of nefopam and is believed to exhibit biological activity.

Moderate to severe pain is often treated using opioids, which are a class of drugs known to have strong analgesic effects in humans. However, opioids have numerous undesirable side effects such as itchiness, sedation, nausea, respiratory depression, constipation, and euphoria. Furthermore, continuous opioid use can lead to dependence often resulting in withdrawal syndrome. Moreover, because of the euphoric effects of opioids, recreational use is common and may lead to accidental overdose and death from respiratory depression. Currently, the United States is experiencing an increase in the rates of recreational use of opioids and addiction, which many attribute to the over-prescription of opioids for pain management.

Accordingly, there is a need for an alternative to opioids in the treatment of pain that is effective as an analgesic but produces fewer side effects, does not produce respiratory depression, and has less abuse potential than opioids. Similarly, there is also a need for effective treatments of pain that allow for reduced doses of opioids to thereby reduce the incidences of side effects and dependency.

SUMMARY OF THE INVENTION

The present invention provides new dosage forms of nefopam, nefopam metabolites, nefopam prodrugs, isomers thereof or combinations of the foregoing that provide a safe and effective alternative to opioids for treating certain types of pain. The present invention also provides new dosage forms of nefopam, nefopam metabolites, nefopam prodrugs, isomers thereof or combinations of the foregoing in combination with one or more other analgesic drugs to thereby allow for a reduced dose of the one or more other analgesic drugs while still providing effective analgesia.

The present invention is directed generally to dosage forms of nefopam, nefopam metabolites, nefopam prodrugs, isomers thereof or combinations of the foregoing including oral solid dosage forms, topical dosage forms, and parenteral formulations. The dosage forms of the present invention may contain nefopam, nefopam metabolites, nefopam prodrugs, isomers thereof or combinations of the foregoing as the sole active ingredient or may contain nefopam, nefopam metabolites, nefopam prodrugs, isomers thereof or combinations of the foregoing in combination with another analgesic drug, such as an opioid analgesic and/or NSAID. The nefopam, nefopam metabolites, nefopam prodrugs, isomers thereof or combinations of the foregoing dosage forms of the present invention may also be administered in combination with an opioid analgesic and/or NSAID.

The present invention may be used to treat pain in humans or animals, i.e., veterinary uses, preferably mammals.

In one embodiment of the present invention, the oral solid dosage form is an enteric-coated formulation of nefopam, nefopam metabolites, nefopam prodrugs, isomers thereof or combinations of the foregoing and optionally an acidic component, such as an organic acid, e.g., citric acid, tartaric acid, fumaric acid, malic acid, etc. that may be used for treating moderate to severe pain. The enteric-coated formulation may also contain a dose of an additional analgesic drug, such as an opioid and/or NSAID.

In another embodiment of the present invention, a parenteral formulation, such as an IV formulation, of nefopam, nefopam metabolites, nefopam prodrugs, isomers thereof or combinations of the foregoing may be used for treating moderate to severe perioperative pain, alone, or as part of a multi-modal patient-controlled analgesia ("PCA") regimen in combination with a dose of an additional analgesic drug, such as an opioid and/or NSAID.

In a further embodiment of the present invention, a topical composition, preferably an unoccluded, adhesive-free topical composition such as a gel, cream, lotion, foam or mousse of nefopam, nefopam metabolite, nefopam prodrug, isomers thereof or combinations of the foregoing, may be used for treating perioperative pain or treating moderate to severe pain associated with graft surgery in patients suffering from skin trauma due to wounds, burns, fasciitis, or cancer. The topical composition may additionally contain a dose of an additional analgesic drug, such as an opioid and/or NSAID, or the additional analgesic drug may be administered separately, such as orally.

In a still further embodiment of the present invention, the nefopam, nefopam metabolite, nefopam prodrug, isomers thereof or combinations of the foregoing is administered alone or in combination with a second pharmaceutically active ingredient through the oral or nasal mucosa.

For example, the nefopam, nefopam metabolite, nefopam prodrug, isomers thereof or combinations of the foregoing may be administered via an orally disintegrating tablet, a sublingual or buccal tablet, an orally disintegrating film, or via an oral or nasal spray.

The present invention is also directed to methods of treating neuropathic pain, including post-herpatic neuralgia, diabetic neuropathic pain, and central neuropathic pain by administering nefopam, nefopam metabolite, nefopam prodrug, isomers thereof or combinations of the foregoing orally or transdermally. The present invention is also directed to methods of treating pain associated with cancer and cancer treatments, as well as methods of treating phantom limb pain.

The dosage forms and methods of the present invention may employ nefopam, nefopam metabolite, nefopam prodrug, isomers thereof or combinations of the foregoing in an amount from about 0.01-1000 mg, preferably 20-120 mg, more preferably 30-90 mg, and most preferably 30-60 mg.

When the dosage forms of the present invention contain, or are administered in combination with, an opioid analgesic and/or NSAID, the dose of the opioid analgesic and/or NSAID may be reduced by about 5-95%, preferably about 20-75%, and most preferably about 50-70% of the normal dose.

DETAILED DESCRIPTION OF THE INVENTION

Except where noted, all terms are intended to have their normal meaning in the art, and are used as they would have been used by a person of ordinary skill at the time of the disclosure. It should be understood that throughout this application the singular forms, such as "a," "an," and "the," are often used for convenience; however, these singular forms are intended to encompass the plural unless otherwise specified, or unless the context clearly calls for the singular alone. It should also be understood that all publication, patents, books, journal articles, and the like, which are referred to in this application, are incorporated by reference in their entirety and for all purposes to the extent not inconsistent with the present disclosure.

"Nefopam" (also known as fenazoxine) refers to the chemical compound (RS)-5-methyl-1-phenyl-1,3,4,6-tetrahydro-2,5-benzoxazocine and has a CAS registry number of 13669-70-0. References to nefopam herein also include its pharmaceutically acceptable salts, such as nefopam hydrochloride. In certain embodiments, the nefopam may be administered as pure or substantially pure, i.e., greater than 90%, preferably greater than 95%, and most preferably greater than 97%, individual isomers, either the (R) or the (S).

"Nefopam metabolite" refers to any compound derived from a mammal's breakdown of nefopam following administration and absorption of nefopam. Representative examples include, but are not limited to, N-desmethyl nefopam and nefopam N-oxide. Unless otherwise indicated, the term "nefopam metabolite" refers to a compound that is isolated and purified outside of a mammal's body and incorporated into a pharmaceutical composition for administration to a mammal via any of the methods described herein. References to nefopam metabolite herein also include its pharmaceutically acceptable salts. In certain embodiments, the nefopam metabolite may be administered as pure or substantially pure, i.e., greater than 90%, preferably greater than 95%, and most preferably greater than 97%, individual metabolite isomers, either the (R) or the (S).

"Nefopam prodrug" refers to any compound that includes the base nefopam structure but which has been modified to include a moiety which can be cleaved or removed by a mammal's, i.e., human's, metabolic system to produce the nefopam molecule or nefopam metabolite following administration of the nefopam prodrug to the mammal. Examples of nefopam prodrugs include, but are not limited to, derivatives of nefopam wherein the methyl moiety on the nitrogen is replaced with an ester, ether, hydroxy, alkoxy, or an alkyl moiety. Alternatively, the phenyl ring may be substituted with an ester moiety, ether moiety, hydroxyl moiety, alkoxy moiety, alkyl moiety or combination thereof. In the context of the term "nefopam prodrug" the term "alkyl" refers to a straight or branched hydrocarbon, preferably a $C_1$-$C_{12}$, except when the alkyl moiety is present on the nitrogen, then "alkyl" refers to a straight or branched hydrocarbon other than a methyl group. In certain embodiments, the nefopam prodrug is a compound wherein the methyl on the nitrogen has been replaced with a carboxylic acid ester moiety such as oxalic acid, malonic acid, malic acid, citric acid, tartaric acid, maleic acid, succinic acid, fumaric acid, glutamic acid, glutaric acid, adipic acid, pimelic acid, suberic acid, azelaic acid, sebacic acid, phthalic acid, isophthalic acid, and terephthalic. Representative examples of nefopam prodrug esters include, but are not limited to, 5-acetate-1-phenyl-1,3,4,6-tetrahydro-2,5-benzoxazocine, 5-ethanoate-1-phenyl-1,3,4,6-tetrahydro-2,5-benzoxazocine, 5-propionate-1-phenyl-1,3,4,6-tetrahydro-2,5-benzoxazocine, 5-butonate-1-phenyl-1,3,4,6-tetrahydro-2,5-benzoxazocine and individual isomers thereof. References to "nefopam prodrug" herein also include its pharmaceutically acceptable salts. In certain embodiments, the nefopam prodrug may be administered as pure or substantially pure, i.e., greater than 90%, preferably greater than 95%, and most preferably greater than 97%, individual prodrug isomers, either the (R) or the (S).

"Substantially similar" means a composition or formulation that resembles the reference composition or formulation to a great degree in both the identities and amounts of the composition or formulation.

"About" means having a value that is sufficiently close to the reference value so as to have identical or substantially identical properties as the reference value. Thus, depending on context, "about" can mean, for example, ±10%, 9%, ±8%, ±7%, ±6, ±5%, ±4%, ±3%, ±2%, ±1%, or ±less than 1%.

"Pharmaceutically acceptable" refers to a material or method that can be used in medicine or pharmacy, including for veterinary purposes for example, in administration to a subject.

"Salt" and "pharmaceutically acceptable salt" includes both acid and base addition salts. "Acid addition salt" refers to those salts that retain the biological effectiveness and properties of the free bases, which are not biologically or otherwise undesirable, and which are formed with inorganic acids and organic acids. "Base addition salt" refers to those salts that retain the biological effectiveness and properties of the free acids, which are not biologically or otherwise undesirable, and which are prepared from addition of an inorganic base or an organic base to the free acid.

"Pharmaceutical formulation" refers to a formulation of a compound of the disclosure and a medium generally accepted in the art for the delivery of the biologically active compound to mammals, e.g., humans. Such a medium includes all pharmaceutically acceptable carriers, diluents and excipients therefor. The pharmaceutical formulations as described herein may be in various dosage forms, such as oral or solid or both dosage forms. In some embodiments, the present pharmaceutical formulations are in tablet or capsule dosage forms.

"Treating" includes ameliorating, mitigating, and reducing the instances of a disease or condition, or the symptoms of a disease or condition. Because the instances of many diseases or conditions can be reduced before the disease or condition manifests, "treating" can also include prophylaxis.

"Administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, and transdermal. "Administering" can also include prescribing or filling a prescription for a dosage form comprising a particular compound. "Administering" can also include providing directions to carry out a method involving a particular compound or a dosage form comprising the compound.

"Administered in combination" and similar phrases as used herein means that nefopam, nefopam metabolite, nefopam prodrug, isomer thereof or combinations of the foregoing is administered with at least one additional pharmaceutically active compound or drug, preferably an opioid analgesic and/or NSAID. The nefopam, nefopam metabolite, nefopam prodrug, isomer thereof or combinations of the foregoing and at least one additional pharmaceutically active compound may be in the same dosage form, such as a tablet containing both pharmaceutically active compounds, or in separate dosage forms that are administered separately. In separate dosage forms, the administration of the separate dosage forms may occur at different times such as a few minutes apart, i.e., within 2-15 minutes, or longer, such as 1-6 hours.

"Effective amount" means the amount of an active substance that, when administered to a subject for treating a disease, disorder, or other undesirable medical condition, is sufficient to have a beneficial effect with respect to that disease, disorder, or condition. The therapeutically effective amount will vary depending on the chemical identity and formulation form of the active substance, the disease or condition and its severity, and the age, weight, and other relevant characteristics of the patient to be treated. Determining the therapeutically effective amount of a given active substance is within the ordinary skill of the art and typically requires no more than routine experimentation.

"Modified release" (also known as MR) includes delayed release (also known as DR) and controlled release (also known as CR, sustained release (SR), prolonged release (PR) or extended release (ER)).

"Delayed release" (also known as DR) relates to a pharmaceutical formulation or component that releases the active ingredients after a period of delay such as after one, two or three hours. One type of DR formulation is an enteric coated formulation that delays the release of the drug from the dosage form until the dosage form encounters an aqueous environment with a pH of 5 or greater.

"Controlled release" (also known as CR) refers to a pharmaceutical formulation or component thereof that releases, or delivers, one or more pharmaceutical agents over a prolonged period of time, in this case over a period of more than one hour.

"Immediate release" (also known as instant release (IR)) refers to a pharmaceutical formulation or component thereof which releases, or delivers, one or more pharmaceutical agents substantially immediately upon administration and will result in substantially complete dissolution within about one hour (or less), preferably less than 45 minutes and most preferably in about 30 minutes or less when tested in a United States Pharmacopeia dissolution apparatus.

"Normal dose" of an opioid analgesic or NSAID means a dose of the opioid analgesic or NSAID that would be recommended for a patient to take or a doctor would prescribe the patient to take if the patient is not taking the opioid analgesic or NSAID in the same dosage form or in combination with nefopam, nefopam metabolite, nefopam prodrug, isomers thereof or combinations of the foregoing. In one aspect, normal doses of an opioid analgesic or NSAID are those doses that have been approved by the U.S. FDA for the particular drug when administered by a particular route. In another aspect, the normal dose of an opioid analgesic or NSAID is a dose that a patient has been taking prior to the initiation of the treatment in the same dosage form or in combination with nefopam, nefopam metabolite, nefopam prodrug, isomers thereof or combinations of the foregoing.

The present invention is directed generally to dosage forms of nefopam, nefopam metabolite, nefopam prodrug, isomers thereof or combinations of the foregoing and optionally one or more acids that further optionally contain an opioid analgesic and/or NSAID, or optionally are administered in combination with an opioid analgesic and/or NSAID.

The acid includes inorganic and organic acids and should be pharmaceutically acceptable. In some embodiments of the present invention the acid is an organic acid, preferably a carboxylic acid. In some embodiments, the carboxylic acid may be a polycarboxylic acid. In another embodiment, the carboxylic acid may be a dicarboxylic acid. Suitable examples of carboxylic acids include, but are not limited to, tartaric acid, adipic acid, succinic acid, citric acid, benzoic acid, acetic acid, ascorbic acid, edetic acid, formic acid, fumaric acid, lactic acid, malic acid, maleic acid, oleic acid, oxalic acid, sorbic acid, stearic acid, palmitic acid, and boric acid, or mixtures thereof. In a preferred embodiment, the acid is a fumaric acid, citric acid, and tartaric acid, or mixtures thereof.

It is believed that the use of a carboxylic acid in combination with nefopam, nefopam metabolite, nefopam prodrug, isomers thereof or combinations of the foregoing aids in the absorption of nefopam, nefopam metabolite, nefopam prodrug, isomers thereof or combinations of the foregoing following oral administration of a solid dosage form such that the resulting formulations yield steadier nefopam, nefopam metabolite, nefopam prodrug, isomers thereof or combinations of the foregoing plasma concentrations. Optimally, administration of a pharmaceutical formulation of the invention releases nefopam, nefopam metabolite, nefopam prodrug, isomers thereof or combinations of the foregoing into the plasma of the patient at a steady or near constant level, i.e., with a low peak-to-trough ratio of nefopam, nefopam metabolite, nefopam prodrug, isomers thereof or combinations of the foregoing plasma concentration, without any significant decrease or fluctuation for an extended amount of time, for example, mimicking infusion administration.

The pharmaceutical formulations of the invention employing a carboxylic acid provide a superior plasma nefopam, nefopam metabolite, nefopam prodrug, isomers thereof or combinations of the foregoing profile to a patient than currently available oral pharmaceutical formulations do. The formulations of the invention are able to provide a significantly smaller peak-to-trough nefopam, nefopam metabolite, nefopam prodrug, isomers thereof or combinations of the foregoing plasma concentration ratio (i.e., narrowing the blood plasma ranges of nefopam, nefopam metabolite, nefopam prodrug, isomers thereof or combinations of the foregoing after the initial peak). Additionally, some embodiments of the pharmaceutical formulations of the invention provide for improvement by increasing the plasma level of nefopam, nefopam metabolite, nefopam prodrug, isomers thereof or combinations of the foregoing. The pharmaceutical formulations of the invention also provide narrow ranges of plasma nefopam, nefopam metabolite, nefopam prodrug, isomers thereof or combinations of the foregoing levels.

The sustained, steady nefopam, nefopam metabolite, nefopam prodrug, isomers thereof or combinations of the foregoing plasma profile of this invention is expected to provide a superior and consistent treatment of pain.

The opioid analgesic that may be formulated with, or administered in combination with the nefopam, nefopam metabolite, nefopam prodrug, isomers thereof or combinations of the foregoing may be one or more compounds selected from base opioid agonists, mixed opioid agonist-antagonists, partial opioid agonists, pharmaceutically acceptable salts, complexes, stereoisomers, ethers, esters, hydrates and solvates thereof and mixtures thereof. Specific opioid drugs suitable for the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts, complexes (e.g., with a cyclodextrin), stereoisomers, ethers, esters, hydrates, solvates, and mixtures thereof.

Preferably, the opioid analgesic is selected from the group consisting of codeine, hydrocodone, hydromorphone, morphine, oxycodone, oxymorphone, tramadol, pharmaceutically acceptable salts, complexes, stereoisomers, ethers, esters, hydrates, solvates, and mixtures thereof.

The NSAID that may be formulated with, or administered in combination with nefopam, nefopam metabolite, nefopam prodrug, isomers thereof or combinations of the foregoing may be aspirin, acetaminophen, ibuprofen, flurbiprofen, ketoprofen, naproxen, oxaprozin, etodolac, indomethacin, ketorolac, lornoxicam, nabumetone, diclofenac, celecoxib, rofecoxib, meloxicam, piroxicam, valdecoxib, parecoxib, or etoricoxib, or combinations thereof. Preferred NSAIDs include, but are not limited to, acetaminophen, ketorolac, diclofenac, celecoxib, and meloxicam.

The present invention is also directed to abuse deterrent/tamper resistant dosage forms of nefopam, nefopam metabolite, nefopam prodrug, isomers thereof or combinations of the foregoing, especially when the dosage form also includes an opioid analgesic. One embodiment of the abuse deterrent dosage forms will include the addition of an opioid antagonist such as naloxone, naltrexone, nalmefene, nalide, nalmexone, nalorphine, nalorphine dinicotinate, cyclazocine, levallorphan, and combinations thereof. Alternative abuse deterrent dosage forms include the use of gelling polymers that make the crushing of the dosage form difficult as well as impede the extraction of the drug from the tampered dosage form and drawing it into a syringe. Another abuse deterrent embodiment includes the incorporation of a nasal irritant into the dosage form to deter tampering and subsequent nasal inhalation.

An embodiment of the present invention relates to oral solid dosage forms comprising a therapeutically effective amount of nefopam, nefopam metabolite, nefopam prodrug, isomers thereof or combinations of the foregoing. The solid oral dosage form may be in the form of a powder, granule, pellet, mini-tablet, tablet, or capsule and comprise the nefopam, nefopam metabolite, nefopam prodrug, isomer thereof or combinations of the foregoing, optionally the acid, and at least one additional pharmaceutically acceptable excipient. The powder, granule, or pellets may be packaged into individual dosing units that provide a therapeutic amount of nefopam, nefopam metabolite, nefopam prodrug, isomers thereof or combinations of the foregoing and allow the user to sprinkle the powder, granules, or pellets onto or into food for administration. The powder, granules, or pellets may also be further processed into mini-tablets, tablets or capsules. Preferably, the oral solid dosage form is a modified release formulation such as delayed release, e.g., enteric, or controlled release mini-tablets, tablets, pellets, or granules. The oral solid dosage forms may be formulated for once-, twice- or thrice-daily administration.

One such embodiment of the present invention is directed to modified release mini-tablets, pellets or granules containing nefopam, nefopam metabolite, nefopam prodrug, isomers thereof or combinations of the foregoing and optionally one or more acids, preferably citric acid, fumaric acid, and/or tartaric acid. The nefopam, nefopam metabolite, nefopam prodrug, isomers thereof or combinations of the foregoing and the acid may be incorporated into the mini-tablets, pellets or granules of the present invention in various manners. For example, the nefopam, nefopam metabolite, nefopam prodrug, isomer thereof or combinations of the foregoing and the acid may be blended together with conventional excipients, such as a polymeric binder, and formed into mini-tablets, pellets or granules. In another embodiment, the dosage form employs a population of nefopam, nefopam metabolite, nefopam prodrug, isomers thereof or combinations of the foregoing-containing mini-tablets, pellets or granules and a separate population of acid-containing mini-tablets, pellets or granules whereby the acid-containing mini-tablets, pellets or granules release the acid according to a similar profile as the nefopam, nefopam metabolite, nefopam prodrug, isomer thereof or combinations of the foregoing-containing mini-tablets, pellets or granules. Each population of mini-tablets, pellets or granules may also include conventional excipients. In another embodiment, the mini-tablets, pellets or granules of the present invention employ a core of the acid and conventional excipients that is surrounded by a layer of nefopam, nefopam metabolite, nefopam prodrug, isomers thereof or combinations of the foregoing and conventional excipients. In a further embodiment, the mini-tablets, pellets or granules of the present invention employ a core of nefopam, nefopam metabolite, nefopam prodrug, isomers thereof or combinations of the foregoing and conventional excipients that is surrounded by a layer of the acid and conventional excipients. In a still further embodiment of the present invention, an inert core is surrounded by separate layers of nefopam, nefopam metabolite, nefopam prodrug, isomers thereof or combinations of the foregoing and the acid. The layered mini-tablets, pellets or granules of the present invention may employ multiple alternating layers of nefopam, nefopam metabolite, nefopam prodrug, isomer thereof or combinations of the foregoing and the acid or single layers of each. It is preferred that the drug layers and acid layers are separated by a water-soluble, rapidly-dispersing barrier layer, which may be any of the water soluble polymers discussed below, and is preferably hydroxypropyl methylcellulose.

Nefopam, nefopam metabolite, nefopam prodrug, isomers thereof or combinations of the foregoing and the acid are present in the pellets in a ratio of from 50:1 to 1:1, preferably 10:1 to 2:1, and more preferably 6:1 to 3:1. The pellets of the present invention may also employ additional drugs such as opioids analgesics and/or NSAIDs. Such additional drugs may be mixed with the nefopam, nefopam metabolite, nefopam prodrug, isomers thereof or combinations of the foregoing and/or acid, present as a separate layer(s), or present as a separate population of pellets.

The core of the pellets may employ an inert carrier, which is typically a starch or sugar sphere having a diameter ranging from about 12-45 mesh, and more preferably from about 35-45 mesh. The inert carrier may be coated by dissolving the nefopam, nefopam metabolite, nefopam prodrug, isomers thereof or combinations of the foregoing or acid in water and then spraying the solution onto the inert carrier using a Wurster insert. Optionally, additional ingredients are also added prior to coating the inert carriers in order to assist in binding. For example, a product which includes hydroxypropyl methylcellulose, etc. with or without colorant (e.g., Opadry®, commercially available from Colorcon, Inc.) may be added to the solution and the solution mixed (e.g., for about 1 hour) prior to application of the same onto the inert carrier. The resultant coated inert carrier may then be optionally overcoated with a barrier agent, to separate the core from any modified release coating.

The cores or layers of the mini-tablets, granules or pellets may also employ a polymeric binder which may be present from 5 to 10 wt % (based on the combined weight of the binder and the drug). Examples of polymeric binders include ethylcellulose, polyvinylpyrrolidone, hydroxypropyl methylcellulose and hydroxypropylcellulose. The binder is applied using conventional solvents which are removed during processing.

The cores or layers of the mini-tablets, granules or pellets may also contain conventional pharmaceutical excipients, for example, a lubricant such as sodium stearate, magnesium stearate, stearic acid, or talc, an anticaking agent such as talc, microcrystalline cellulose, starch, metallic stearates, or a divalent silicate, a glidant such as silicon dioxide, and/or a polymeric material that is rapidly soluble in water or, alternatively, may be freely permeable to the drug and/or acid and water, for example, polyvinyl alcohol, polyvinylpyrrolidone, methyl cellulose, hydroxypropyl cellulose, hydroxypropylmethyl cellulose, EUDGRAGIT RL, or polyethylene glycol, or a mixture thereof. In some embodiments of the present invention, the water soluble polymer, if employed as a seal-coating or a coating separating the nefopam, nefopam metabolite, nefopam prodrug, isomers thereof or combinations of the foregoing and acid, has a molecular weight of less than 100,000, preferably less than 50,000. In some embodiments, the water soluble polymer exhibits a viscosity at room temperature when a 2% water solution is formed with the polymer of less than 25 cps, preferably less than 15 cps, and most preferably less than 10 cps. The core may additionally include further components such as a dispersing agent, glidant, acidifying agent to maintain optimum pH, diluent, antimicrobial preservative, antioxidant, and/or surfactant. The conventional excipient(s) may be blended with the nefopam, nefopam metabolite, nefopam prodrug, isomers thereof or combinations of the foregoing, opioid, NSAID, or acid using standard dry mixing techniques as is known in the art.

The mini-tablets, granules, pellets, or cores of the present invention may also include one or more modified release layers, such as an enteric coating or controlled release coating or combination thereof. In an embodiment, the dosage form may employ separate populations of immediate release mini-tablets, granules or pellets, delayed release mini-tablets, granules or pellets, and/or controlled release mini-tablets, granules or pellets, or a combination thereof, to achieve a desired release profile.

The mini-tablets, granules or pellets may be provided with an enteric coating that is a polymeric enteric coating material. The enteric coatings are "pH dependent," meaning that the enteric coating prevents release of the dosage form in the low pH conditions of the stomach but permits release in the higher pH conditions of the small intestine. The enteric coating may be present from 4 to 10%, preferably from 5 to 8%, by weight based on the combined weight of the mini-tablet, granule or pellet component and the total weight of the coating. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate and polyvinyl acetate phthalate. The thickness of the coating is selected to provide the desired release rate depending on the thickness of the coating and the particular coating.

A commercially available copolymer is Eudragit® S100 which is based on methacrylic acid and methyl methacrylate and has a weight average molecular weight of about 150,000. Other auxiliary coating aids such as a minor amount (1-15 wt % based on the pellet component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 200 to 1,000, preferably 300-600), propylene glycol and mixtures thereof in combination with an antisticking agent which may be a silicate such as talc. The antisticking agent may be added in an amount which is equivalent to 0.3 to 1.0:1.0 by weight of the methacrylic acid copolymer. These components may be added to the methacrylic acid copolymer in combination with appropriate solvents.

The mini-tablet, granules or pellets may also be provided with a controlled or sustained release coating. A non-limiting list of suitable controlled-release materials which may be included in a controlled-release coating according to the invention include hydrophilic and/or hydrophobic materials, such as gums, cellulose ethers, acrylic resins, protein derived materials, waxes, shellac, and oils such as hydrogenated castor oil, hydrogenated vegetable oil. However, any pharmaceutically acceptable hydrophobic or hydrophilic controlled-release material which is capable of imparting controlled-release of the nefopam, nefopam metabolite, nefopam prodrug, isomers thereof or combinations of the foregoing, may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polymethacrylate, polyacrylamide, poly(methacrylic acid anhydride), and glycidyl methacrylate copolymers. Certain preferred embodiments utilize mixtures of any of the foregoing controlled-release materials in the coatings of the invention.

The modified release coating may be applied to the mini-tablet, granules or pellets using methods and techniques known in the art. Typically a suspension, emulsion, or solution of the polymeric coating is prepared as is known in the art. The amount of fluidized polymeric coating required in the coating process may be readily calculated depending upon the amount of polymeric coating desired in the dried mini-tablet, granules or pellets. The fluid polymeric coating may be applied to the mini-tablet, granule or pellet by a number of coating techniques known in the art. Examples of suitable coating devices include fluid bed coaters, pan coaters, etc.

In a preferred embodiment, the mini-tablets, granules or pellets may be overcoated with an aqueous dispersion of the modified release material. The aqueous dispersion of the modified release material preferably further includes an effective amount of plasticizer, e.g., tri-ethyl citrate.

The plasticized aqueous dispersion of modified release material may be applied onto the mini-tablets, granules or pellets by spraying, using any suitable spray equipment known in the art. In a preferred method, a Wurster fluidized-bed system is used, in which an air jet, injected from underneath, fluidizes the core material and effects drying while the acrylic polymer coating is sprayed on. A sufficient amount of the aqueous dispersion of modified-release material to obtain a predetermined modified-release of the therapeutically active agent when said coated mini-tablet, granule or pellet is exposed to aqueous solutions, e.g., gastric fluid, is preferably applied, taking into account the physical characteristics of the therapeutically active agent, the manner of incorporation of the plasticizer, etc. After coating with the modified-release material, a further overcoat of a film-former, such as Opadry®, is optionally applied to the mini-tablets, granules or pellets. This overcoat is provided, if at all, in order to substantially reduce agglomeration of the particles.

The powder, granules, mini-tablets or pellets may be filled into hard or soft gelatin capsules or packaged into individual dosing unites, e.g., sachets. The powders, granules, mini-tablets, or pellets may also be compressed into tablets using a binder and/or hardening agent commonly employed in tableting such as microcrystalline cellulose sold under the Trademark "AVICEL" or a co-crystallized powder of highly modified dextrins (3% by weight) and sucrose sold under the Trademark "DI-PAC" in such a way that the specific dissolution rate of the individual pre-compression particles is maintained. The powders, granules, mini-tablets or pellets in the capsules or individual dosing units may be sprinkled onto food such as applesauce or dispersed into water for easier administration to patients that have difficulty swallowing a large capsule or tablet.

Another embodiment of the present invention is directed to modified release tablets containing a therapeutically effective amount of nefopam, nefopam metabolite, nefopam prodrug, isomers thereof or combinations of the foregoing, optionally one or more of the acids mentioned above, and optionally an opioid analgesic and/or NSAID. Suitable tablets in accordance with the present invention include enteric tablets, osmotic tablets, and matrix tablets.

The enteric tablets according to the present invention employ a core element that is preferably a compressed tablet that comprises nefopam, nefopam metabolite, nefopam prodrug, isomers thereof or combinations of the foregoing, optionally an acid, and conventional excipients. The core element is surrounded by an enteric coating. The core may also optionally include an opioid analgesic or NSAID.

The core element is preferably manufactured by first passing all of the dry ingredients through a screen (e.g., 300 mesh USSS) and thereafter tumble blending the dry ingredients for 5 to 120 minutes to form a compressible powder blend. The compressible powder blend is preferably pressed into tablets using an automatic tableting machine provided with a suitable die.

In another embodiment, the core element employs separate layers of nefopam, nefopam metabolite, nefopam prodrug, isomers thereof or combinations of the foregoing, the acid, and optional opioid analgesic and/or NSAID. Each layer may be manufactured by preparing separate powder blends, as described above, and then pressing the separate blends together into a bilayer or trilayer tablet.

The enteric coating may be any of the polymeric enteric coating materials mentioned above. The enteric coating may comprise from 1 to 10%, preferably 1 to 6%, and most preferably from 2 to 4% by weight based on the combined weight of the tableted core and the coating. Other auxiliary coating aids such as a minor amount (1-15 wt % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 200 to 1,000, preferably 300-600), propylene glycol and mixtures thereof in combination with an antisticking agent which may be a silicate such as talc. The antisticking agent may be added in an amount which is equivalent to 0.3 to 1.0:1.0 by weight of the enteric coating polymer. These components may be added to the enteric coating polymer in combination with appropriate solvents.

A further embodiment of the present invention is directed to osmotic tablets that may contain a homogenous core or a multilayer core such as a bilayer core comprising a drug layer and a delivery or push layer, wherein the core is surrounded by a semipermeable wall and optionally having at least one passageway disposed therein. In certain embodiments, the homogeneous core comprises the nefopam, nefopam metabolite, nefopam prodrug, isomer thereof or combinations of the foregoing, a hydrogel, and optionally additional pharmaceutically acceptable excipients such as an acid. A hydrogel as used herein is a natural or synthetic compound that absorbs water when exposed to an aqueous environment and expands to at least twice its unhydrated volume. Examples of hydrogels are provided below. The homogeneous core is prepared by mixing and or granulating the core ingredients to obtain a uniform blend and compressing the uniform blend into a tablet core. In another embodiment, the bilayer core comprises a drug layer with nefopam, nefopam metabolite, nefopam prodrug, isomer thereof or combinations of the foregoing and a displacement or push layer. In other embodiments, the osmotic tablets employ a trilayer core that comprises a drug layer of nefopam, nefopam metabolite, nefopam prodrug, isomer thereof or combinations of the foregoing, an additional drug layer of an opioid analgesic and/or NSAID, and a displacement or push layer between the drug layers. In such an embodiment, the semipermeable wall surrounding the trilayer core may optionally have at least two passageways disposed therein, with at least one passageway adjacent the nefopam, nefopam metabolite, nefopam prodrug, isomers thereof or combinations of the foregoing drug layer and at least one passageway adjacent the opioid/NSAID drug layer. In certain embodiments the drug layer(s) may also comprise at least one polymeric hydrogel. The polymeric hydrogel employed in the drug layer may have an average molecular weight of between about 500 and about 6,000,000. Examples of polymeric hydrogels employed in the drug layer include but are not limited to a maltodextrin polymer comprising the formula $(C_6H_{12}O_5)_n \cdot H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight. Additional examples of hydrogels include natural and synthetic gums.

In certain embodiments of the present invention, the delivery or push layer comprises a hydrogel or gelling polymer. Examples of hydrogels for use in the delivery or push layer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. The carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The hydrogels used for the displacement layer should exhibit an osmotic pressure gradient across the semipermeable wall. The hydrogels imbibe fluid into dosage form, thereby swelling and expanding, whereby they push the nefopam, nefopam metabolite, nefopam prodrug, isomers thereof or combinations of the foregoing or opioid/NSAID from the osmotic dosage form.

The push layer may also include one or more osmotically effective compounds, also known as osmagents and as osmotically effective solutes. They imbibe an environmental fluid, for example, from the gastrointestinal tract, into dosage the form and contribute to the delivery kinetics of the displacement layer. Examples of osmotically active compounds include members selected from the group consisting of osmotic salts and osmotic carbohydrates. Examples of specific osmagents include, but are not limited to, sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose represented by a member selected from the group consisting of hydroxypropylmethylcellulose, hydroxypropylethylcellulose, hydroxypropylisopropylcellulose, hydroxypropylbutylcellulose, and hydroxypropylpentylcellulose. Depending upon the type and molecular weight, the hydroxypropylalkylcellulose may also be a hydrogel.

The push layer may also optionally comprise an antioxidant to inhibit the oxidation of ingredients. Some examples of antioxidants include, but are not limited to, members selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain embodiments, the semipermeable wall comprises a member selected from the group consisting of a cellulose ester polymer, a cellulose ether polymer and a cellulose ester-ether polymer. Representative wall polymers comprise members selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate, semipermeable polyamide, semipermeable polyurethane, semipermeable sulfonated polystyrene, semipermeable cross-linked polymer formed by the coprecipitation of a polyanion and a polycation as disclosed in U.S. Pat. Nos. 3,173,876; 3,276,586; 3,541,005; 3,541,006 and 3,546,876, semipermeable polymers as disclosed by Loeb and Sourirajan in U.S. Pat. No. 3,133,132, semipermeable crosslinked polystyrenes; semipermeable cross-linked poly(sodium styrene sulfonate), semipermeable crosslinked poly(vinylbenzyltrimethyl ammonium chloride), and semipermeable polymers possessing a fluid permeability of $2.5 \times 10^{-8}$ to $2.5 \times 10^{-2} (cm^2/hr\ atm)$ expressed per atmosphere of hydrostatic or osmotic pressure difference across the semipermeable wall. Other polymers useful in the present invention and known in the art are described in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, the semipermeable wall is preferably nontoxic, inert, and it maintains its physical and chemical integrity during the dispensing life of the drug. In certain embodiments, the dosage form comprises a binder as described above.

In certain embodiments, the dosage form comprises a lubricant, which may be used during the manufacture of the dosage form to prevent sticking to die wall or punch faces. Examples of lubricants include, but are not limited to, magnesium stearate, sodium stearate, stearic acid, calcium stearate, magnesium oleate, oleic acid, potassium oleate, caprylic acid, sodium stearyl fumarate, and magnesium palmitate.

An additional embodiment of the present invention is direct to a controlled-release matrix tablet. The matrix tablet should comprise a therapeutically effective amount of the nefopam, nefopam metabolite, nefopam prodrug, isomers thereof or combinations of the foregoing, a matrix forming agent, optionally an acid and optionally an opioid and/or NSAID. The matrix forming agent can be a hydrophobic material such as a wax, a hydrophilic material such as a hydrogel, or a combination of the two. The matrix forming agent will control the release of the nefopam, nefopam metabolite, nefopam prodrug, isomers thereof or combinations of the foregoing and optionally the acid or opioid/NSAID, if present, by diffusion from the matrix, erosion of the matrix, or a combination of diffusion and erosion. The amount of diffusion and erosion will depend upon the materials selected for the formation of the matrix.

Examples of hydrogels that may be used for the matrix forming agent include those previously described, and preferably hydroxypropyl methylcellulose, carboxymethylcellulose calcium, carboxymethylcellulose sodium, guar gum, hydroxyethyl cellulose, hydroxypropyl cellulose, methyl cellulose, acrylic polymers and copolymers, sodium alginate, polyethylene oxides or mixtures thereof.

Examples of hydrophobic materials that can be used for the matrix forming agent include beeswax, white wax, emulsifying wax, hydrogenated vegetable oil, hydrogenated castor oil, microcrystalline wax, cetyl alcohol, stearyl alcohol, free wax acids such as stearic acid, esters of wax acids, propylene glycol monostearate, glycerol monostearate, carnauba wax, palm wax, candelilla wax, lignite wax, ozokerite, ceresin wax, lardaceine, China wax and mixtures thereof. Other possible rate controlling excipients useful in the present invention include saturated hydrocarbons having from 25 to 31 carbon atoms, saturated alcohols having from 25 to 31 carbon atoms, saturated monocarboxylic acids having from 25 to 31 carbon atoms, esters obtained from said alcohols and monocarboxylic acids which are described in U.S. Pat. No. 6,923,984, incorporated herein by reference.

A combination of hydrophobic and hydrophilic materials may also be used in preparing a controlled release matrix of the present invention.

The controlled release matrix in accordance with the present invention may further comprise conventional excipients that improve processing or modify the release characteristics. Examples of these conventional excipients include fillers, glidants and lubricants described previously.

Some embodiments of the controlled release matrix tablets may include a multilayer tablet wherein at least one layer is a controlled release matrix comprising nefopam, nefopam metabolite, nefopam prodrug, isomers thereof or combinations of the foregoing, the matrix forming agent, optionally an acid, and optionally an opioid and/or NSAID. Alternatively, the multilayer tablet may comprise at least one controlled release layer comprising nefopam, nefopam metabolite, nefopam prodrug, isomers thereof or combinations of the foregoing, the matrix forming agent, optionally an acid and at least one separate and distinct controlled release layer comprising an opioid and/or NSAID and a matrix forming agent. The multilayer tablet embodiments may further comprise an immediate release layer that comprises an immediate release dose of nefopam, nefopam metabolite, nefopam prodrug, isomers thereof or combinations of the foregoing and/or an immediate release dose of an opioid and/or NSAID.

Delayed release oral solid dosage forms in accordance with the present invention, and described above (i.e., pellets or tablets), should exhibit an in vitro dissolution profile when measured in 0.1N HCl in a USP XXII Type II apparatus at 37° C. and 100 rpm that substantially corresponds to the following:
a) from 0 to 30%, preferably from 0 to 25%, and most preferably from 0 to 20% of total nefopam, nefopam metabolite, nefopam prodrug, isomers thereof or combinations of the foregoing is released after 2 hours.

Delayed release oral solid dosage forms in accordance with the present invention, and described above (i.e., pellets or tablets), should also exhibit an in vitro dissolution profile when measured in an aqueous medium with a pH of 6.0 or greater, preferably 6.8 in a USP XXII Type II apparatus at 37° C. and 100 rpm that substantially corresponds to the following:
a) from 50 to 100%, preferably from 75 to 100%, and most preferably from 90 to 100% of total nefopam, nefopam metabolite, nefopam prodrug, isomers thereof or combinations of the foregoing is released after 2 hours.

Controlled release oral solid dosage forms in accordance with the present invention, and described above (i.e., pellets or tablets), for once daily dosing preferably exhibit an in vitro dissolution profile when measured in 0.1N HCl in a USP XXII Type II apparatus at 37° C. and 100 rpm which substantially corresponds to the following:
a) from 0 to 30% and preferably from 5 to 25% of total nefopam, nefopam metabolite, nefopam prodrug, isomers thereof or combinations of the foregoing is released after 2 hours;
b) from 25 to 70% and preferably from 35 to 65% of total nefopam, nefopam metabolite, nefopam prodrug, isomers thereof or combinations of the foregoing is released after 12 hours;
c) from 50 to 90% and preferably from 60 to 85% of total nefopam, nefopam metabolite, nefopam prodrug, isomers thereof or combinations of the foregoing is released after 18 hours;
d) not less than 95% and preferably not less than 99% of total nefopam, nefopam metabolite, nefopam prodrug, isomers thereof or combinations of the foregoing is released after 24 hours.

Controlled release oral solid dosage forms in accordance with the present invention, and described above (i.e., pellets or tablets), for twice daily dosing preferably exhibit an in vitro dissolution profile when measured in 0.1N HCl in a USP XXII Type II apparatus at 37° C. and 100 rpm which substantially corresponds to the following:
a) from 0 to 45% and preferably from 10 to 40% of total nefopam, nefopam metabolite, nefopam prodrug, isomers thereof or combinations of the foregoing is released after 2 hours;
b) from 25 to 75% and preferably from 35 to 70% of total nefopam, nefopam metabolite, nefopam prodrug, isomers thereof or combinations of the foregoing is released after 6 hours;
d) not less than 95% and preferably not less than 99% of total nefopam, nefopam metabolite, nefopam prodrug, isomers thereof or combinations of the foregoing is released after 12 hours.

If the controlled release oral solid dosage form for once-, twice-, or thrice-daily dosing is a multiparticulate formulation comprising a plurality of nefopam, nefopam metabolite, nefopam prodrug, isomers thereof or combinations of the foregoing-containing mini-tablets, granules and/or pellets, the multiparticulate formulation may comprise immediate release powder, granules, mini-tablets, granules and/or pellets, delayed release granules, mini-tablets, granules and/or pellets, and/or controlled release granules, mini-tablets, granules and/or pellets that are blended together to obtain the desired release profile.

The oral solid dosage forms in accordance with the present invention, particularly those that also include an opioid, may further include abuse deterrent/tamper resistant features.

In one embodiment, the dosage form additionally comprises a bittering agent to discourage an abuser from tampering with the dosage form and thereafter inhaling or swallowing the tampered dosage form. Preferably, the bittering agent is released when the dosage form is tampered with and provides an unpleasant taste to the abuser upon inhalation and/or swallowing of the tampered dosage form. Suitable bittering agents include natural, artificial and synthetic flavor oils and flavoring aromatics and/or oils, oleoresins and extracts derived from plants, leaves, flowers, fruits, and so forth, and combinations thereof. Non-limiting representative flavor oils include spearmint oil, peppermint oil, *eucalyptus* oil, oil of nutmeg, allspice, mace, oil of bitter almonds, menthol and the like. Also useful bittering agents are artificial, natural and synthetic fruit flavors such as citrus oils including lemon, orange, lime, grapefruit, and fruit essences and so forth. Additional bittering agents include sucrose derivatives (e.g., sucrose octaacetate), chlorosucrose derivatives, quinine sulphate, and the like. A further bittering agent for use in the present invention is Denatonium Benzoate NF-Anhydrous sold under the name Bitrex™ (Macfarlan Smith Limited, Edinburgh, UK). A bittering agent may be added to the formulation in an amount of less than about 50% by weight, preferably less than about 10% by weight, most preferably less than about 5% by weight of the dosage form, and most preferably in an amount ranging from about 0.1 to 1.0 percent by weight of the dosage form depending on the particular bittering agent(s) used.

In another embodiment, the dosage form additionally comprises an irritant to discourage an abuser from tampering with the dosage form and thereafter inhaling, injecting, or swallowing the tampered dosage form. Preferably, the irritant is released when the dosage form is tampered with and provides a burning or irritating effect to the abuser upon inhalation, injection, and/or swallowing the tampered dosage form. Suitable irritants include capsaicin, a capsaicin analog with similar type properties as capsaicin, and the like. Some capsaicin analogues or derivatives include for example and without limitation, resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide, or other compounds of the class known as vanilloids. In a particular embodiment, capsaicin or analogues thereof are employed in a concentration between about 0.00125% and 50% by weight, preferably between about 1 and about 7.5% by weight, and most preferably, between about 1 and about 5% by weight.

In a further embodiment, the dosage form additionally comprises a gelling agent to discourage an abuser from tampering with the dosage form and thereafter inhaling, injecting, or swallowing the tampered dosage form. Preferably, the gelling agent is released when the dosage form is tampered with and provides a gel-like quality to the tampered dosage form which slows the absorption of the opioid analgesic such that an abuser is less likely to obtain a rapid "high". In certain preferred embodiments, when the dosage form is tampered with and exposed to a small amount (e.g., less than about 10 ml) of an aqueous liquid (e.g., water), the dosage form will be unsuitable for injection and/or inhalation. Upon the addition of the aqueous liquid, the tampered dosage form preferably becomes thick and viscous, rendering it unsuitable for injection. Suitable gelling agents include the previously described hydrogels as well as sugars or sugar derived alcohols, such as mannitol, sorbitol, and the like, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof. A gelling agent may be added to the dosage form in a ratio of gelling agent to opioid of from about 1:40 to about 40:1 by weight, preferably from about 1:1 to about 30:1 by weight, and more preferably from about 2:1 to about 10:1 by weight of the opioid.

In another embodiment, the dosage form further comprises an opioid antagonist. The opioid antagonist preferably has low oral bioavailability. The opioid antagonist may also be sequestered, i.e., in a non-releasable form when taken orally and the dosage form has not been tampered with. The sequestered opioid agonist may be present as coated particles or in a matrix that employs a hydrophobic material. Suitable hydrophobic materials include cellulose polymers selected from the group consisting of ethylcellulose, cellulose acetate, cellulose propionate (lower, medium or higher molecular weight), cellulose acetate propionate, cellulose acetate butyrate, cellulose acetate phthalate and cellulose triacetate. Suitable opioid antagonists include naloxone, naltrexone, nalmefene, nalide, nalmexone, nalorphine, nalorphine dinicotinate, cyclazocine, levallorphan, and combinations thereof.

Another embodiment of the present invention is directed to orally-disintegrating films, preferably rapidly-dissolving orally-disintegrating films that contain nefopam, nefopam metabolite, nefopam prodrug, isomers thereof or combinations of the foregoing and optionally an additional active agent, such as an opioid analgesic and/or NSAID, and optionally an acid. Preferably the active agent(s) are taste-masked or controlled-release particles uniformly distributed through the film. The films of the present invention are suitable for oral, sublingual, or buccal administration.

The films of the present invention may be formed by wet casting methods and hot melt extrusion methods as known in the art. In a wet casting method, the film product is formed by combining a polymer and a polar solvent, forming the combination into a film, and drying the film in a controlled manner. Preferably, the film is dried initially by only applying heat to the bottom side of the film, in order to maintain a non-self-aggregating uniform heterogeneity. Desirably, during the initial bottom drying stage, substantially no convection currents, i.e., hot air currents, are permitted to travel across the top of the film until the visco-elastic properties of the film are such that the film components are "locked" in place and cannot move to cause non-uniformity. At that stage, other methods of heating to effect drying may be employed.

The films of the present invention may be formed with a polar solvent which may be water, a polar organic solvent, or a combination thereof. The active ingredient(s) may be added to the polymer and water combination prior to the drying step. Alternatively, or in addition to controlling the drying the film, the polymer may be selected in order to provide a viscosity that maintains the non-self-aggregating uniform heterogeneity. Moreover, the composition desirably is mixed in a manner to minimize the incorporation of air into the mixture and is desirably deaerated, such as by conditioning at room temperature, vacuum treatment or the like, to allow trapped air to escape prior to the drying process. Reverse roll coating is one particularly useful coating technique may also be used to form the film.

In an embodiment, the film contains at least one water-soluble polymer including polyethylene oxide alone or in combination with a hydrophilic cellulosic polymer, wherein the film product may be free of added plasticizers. Preferably, the rapid-dissolve film product includes at least one water-soluble polymer containing about 20% to 100% by weight polyethylene oxide, about 0% to 80% by weight hydroxypropylmethyl cellulose, and about 0% to 80% by weight hydroxypropyl cellulose, an active component, sweetener, at least one flavoring, and at least one colorant, wherein the film product optionally is free of added plasticizers, surfactants, and polyalcohols.

In another aspect of the present invention, the films employing polyethylene oxide as the film-forming polymer may be formed by a hot melt extrusion process, whereby an edible film-forming polymer is provided, and active component(s) are added during manufacture, and the mixture is blended at elevated temperature in the absence of additional solvent to form a uniform matrix, and extruded to form a film. Desirably, the film will be further shaped by rollers to a specified thickness, and allowed to cool and harden to form a self-supporting film. A particularly desirable film forming polymer for extrusion manufacture is polyethylene oxide, which is heated to from about 65° C. to about 80° C. during blending to provide a pliable uniform matrix. The extrusion may be accomplished with a single screw extrusion apparatus or other suitable extrusion apparatus.

Another aspect of the present invention provides films containing coated particles that include an active agent(s) and a taste-masking and/or controlled-release coating. Accordingly, there is provided a drug delivery composition that includes (i) a flowable water-soluble film forming matrix, (ii) a particulate active agent(s) uniformly stationed therein, and (iii) a taste-masking agent or controlled-release agent coated or intimately associated with the particulate to provide taste-masking of the active agent(s). In some embodiments, the combined particulate and taste-masking agent have a particle size of 200 microns or less and the flowable water-soluble film forming matrix is capable of being dried without loss of uniformity in the stationing of the active agent(s) therein.

In an embodiment, the taste-masking or controlled-release coated particles may have a particle size of 50 to 250 microns, and the flowable water-soluble film forming matrix is capable of being dried without loss of uniformity in the stationing of the particulate active agent(s) therein.

Preferable, the size of the combined particulate and taste-masking agent is a particle size of 150 microns or less, or 100 microns or less. The flowable water-soluble film forming matrix is formable into a dry film of less than about 380 microns in thickness, for example, less than about 250 microns in thickness. Preferably, the coated particles are embedded entirely within the finished films.

Preferably, the taste-masking or controlled-release agent is a thin film coating over portions of the active agent(s). Useful taste-masking agents include polymeric materials. Water-soluble polymers are also useful. Preferably, the water-soluble polymer has an average molecular weight of equal to or greater than about 40,000. Furthermore, water-soluble polymers may be acrylic polymers, cellulosic polymers, and combinations thereof. Additionally, vinyl polymers, crown ethers, hydrogenated oils and waxes, and combinations thereof may also be used as taste-masking agents.

In an embodiment of the present invention, the film composition includes: (a) an edible water-soluble film forming matrix, and (b) a coated particulate active component uniformly stationed therein, wherein the coating on the particulate active component is a taste-masking or controlled-release agent and wherein the coated particulate active component has a particle size of 50 to 250 microns and is uniformly distributed in the film composition.

In another embodiment of the present invention, the film composition includes: (a) an edible water-soluble film forming matrix including at least one water-soluble polymer including polyethylene oxide alone or in combination with a hydrophilic cellulosic polymer, and (b) a coated particulate active component uniformly stationed therein, wherein the coating on the particulate active component is a taste-masking and/or controlled-release agent, and wherein the active component is uniformly distributed in the film composition.

The film forming polymers useful for the films of the present invention may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

A further embodiment of the present invention is directed to an orally disintegrating tablet ("ODT") that contains nefopam, nefopam metabolite, nefopam prodrug, isomers thereof or combinations of the foregoing, optionally one or more additional active agents, such as an opioid analgesic and/or an NSAID, and optionally an acid. The ODT of the present invention rapidly dissolves when placed in a patient's oral cavity, sublingual area, or buccal cavity.

In an embodiment, the active agent(s) are present in the ODT as coated particles, i.e., granules or pellets. The particles can be coated with a coating composition comprising at least one coating polymer selected from the group consisting of cellulosic polymers, acrylic polymers and their mixtures. Among the cellulosic polymers, ethylcellulose, hydroxypropylcellulose (HPC) and hydroxypropylmethyl-cellulose (HPMC), can be used. Among the acrylic polymers, insoluble acrylate ammonio-methacrylate copolymer (Eudragit™ RL100 or RS100 or Eudragit™ RL30D or RS30D), polyacrylate (Eudragit™ NE30D), or methacrylic copolymers (e.g., Eudragit™ L100-55 Eudragit™ L30D, Eudragit™ E100 and Eudragit™ EPO) can be used, alone, in combination, or in admixture with pH-dependent polymers. Eudragit™ E100 or a mixture of Eudragit™ EPO and Eudragit™ NE30D are suitably used.

The ODTs of the present invention additionally comprise at least one sugar alcohol. Examples of sugar alcohols that may be used in the present invention include arabitol, mannitol, sorbitol, dextrose, dextrin, sucrose, maltose, xylitol, maltitol, lactitol, erythritol, isomalt and mixtures thereof.

The ODTs of the present invention may further comprise conventional pharmaceutically acceptable excipients such as lubricants, fillers, binders, disintegrants, glidants, solubilizing agents, flavoring agents, gas producing agents, pH adjusting agents, antioxidants, chelating agents, or mixtures of the foregoing. The amount of these excipients present in the solid dosage forms will vary depending upon the specific and desired properties of the solid dosage form. Ranges and amounts of these excipients are known and reported in literature known in the art. In certain embodiments, the disintegrating agent is selected from the group consisting of croscarmellose, available as e.g. Ac-di-sol™, crospovidone available as e.g. Kollidon CL™ sodium starch glycolate and mixtures thereof.

The ODTs of the present invention may be prepared by any method known in the pharmaceutical arts such wet granulation, slugging and/or dry mixing the active ingredient(s) with the selected excipients and forming the granules, aggregates or mixtures into tablets.

In certain embodiments of the present invention, the ODTs exhibits a friability of less than 2%, preferably less than 1.5%, and most preferably less than 1.0%.

In certain embodiments of the present invention, the ODTs should dissolve in a patient's oral cavity or in a United States Pharmacopeia (USP) Disintegration test in less than 2.5 minutes, preferably less than 2.0 minutes, and most preferably less than 1.5 minutes.

An additional embodiment of the present invention is directed to oral or nasal sprays that comprise nefopam, nefopam metabolite, nefopam prodrug, isomers thereof or combinations of the foregoing, optionally an additional active ingredient, such as an opioid analgesic and/or NSAID, and optionally an acid. The oral and nasal sprays of the present invention are in the form of a liquid, preferably a solution of suspension. In addition to nefopam, nefopam metabolite, nefopam prodrug, isomer thereof or combinations of the foregoing, the liquids may contain inert diluents and/or solvents commonly used in the art. Water is the preferred solvent, however, combinations of water with other physiologically acceptable solvents as required are also contemplated. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as polyethylene glycols, and surfactants/emulsifiers like the fatty acid esters of sorbitan, and mixtures thereof. Oils, in particular, cottonseed, peanut, or corn oils, may also be added to the compositions. The combination of the additional solvents in the aqueous solution should preferably not exceed about 15% (w/v) of the total composition. Besides inert diluents, the oral compositions can also include adjuvants such as wetting agents, emulsifying and suspending agents (e.g., microcrystalline cellulose, sodium carboxymethyl cellulose, hypromellose, carbopol and the like), surfactants, sweetening, flavoring, and perfuming agents. The liquids that provide the nefopam, nefopam metabolite, nefopam prodrug, isomer thereof or combinations of the foregoing in suspension may comprise, in addition to nefopam, nefopam metabolite, nefopam prodrug, isomer thereof or combinations of the foregoing, one or more suspending agents such as microcrystalline cellulose, magnesium aluminum silicate, bentonite, agar-agar, hypromellose, sodium carboxymethyl cellulose, carbopol/carbomer, pectin, acacia, tragacanth or mixtures thereof.

The liquid compositions of the present invention may further comprise one or more preservatives and/or one or more stabilizers. Preservatives that are suitable for use in the compositions of the invention include, but are not limited to, edetic acid and their alkali salts such as disodium EDTA and calcium EDTA, benzyl alcohol, methylparaben, propylparaben, butylparaben, chlorobutanol, phenylethyl alcohol, benzalkonium chloride, thimerosal, propylene glycol, sorbic acid, and benzoic acid derivatives. The preservatives should be used at a concentration of from about 0.001% to about 0.5% (w/v) in the final composition. The combination of benzalkonium chloride, used at a concentration of from about 0.001% to about 0.5% or preferably from about 0.005% to about 0.1% (w/v), and edetic acid (as a disodium salt), used at a concentration of from about 0.005% to about 0.1% (w/v), are the preferred preservative/stabilizer combination used in the liquid compositions of the present invention.

Certain compositions of the invention may further comprise one or more solubility-enhancing agents that are used to improve the solubility of the nefopam, nefopam metabolite, nefopam prodrug, isomer thereof or combinations of the foregoing. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, and polyethylene glycols (molecular weights of 200 to 600).

Certain compositions of the invention may further comprise one or more agents that are used to render the composition isotonic, particularly in those compositions in which water is used as a solvent. Such agents are particularly useful in compositions formulated for nasal or ocular application, since they adjust the osmotic pressure of the formulations to the same osmotic pressure as nasal or ocular secretions. Agents that are suitable for such a use in the compositions of the invention include, but are not limited to, sodium chloride, sorbitol, propylene glycol, dextrose, sucrose, and glycerine, and other isotonicity agents that are known in the art (see, e.g., Reich et al., "Chapter 18: Tonicity, Osmoticity, Osmolality and Osmolarity," in: *Remington: The Science and Practice of Pharmacy*, 20$^{th}$ Edition, Lippincott Williams and Wilkins, Philadelphia, Pa. (2000)).

It is desirable that the compositions of the present invention that are to be administered in liquid form have a pH of about 4.5 to about 7.4, and preferably have a pH of about 5.5 to 7.1, for physiological reasons. Accordingly, in additional embodiments, the compositions of the invention may further comprise one or more buffering agents that are used to adjust and/or maintain the compositions in the desired pH range. Adjustment of pH or buffering agents that are suitable for use in the compositions of the invention include, but are not limited to, citric acid, sodium citrate, sodium phosphate (dibasic, heptahydrate form), and boric acid or equivalent conventional buffers, or combinations thereof. The appropriate amounts of buffers and buffering agents, or combinations thereof, that are to be used in the compositions of the invention are described in the United States Pharmacopoeia, *Remington: The Science and Practice of Pharmacy*, and the like, the disclosures of which are incorporated herein by reference in their entireties.

The liquid formulations of the invention preferably further comprise one or more taste-masking agents, one or more flavoring agents, and/or one or more sweetening agents, or a combination of such agents.

In an embodiment of the invention, the liquid compositions may further comprise one or more water-soluble viscosity-increasing agents. Such agents are preferably used at the concentration of about 0.01% to about 5.0% (w/v), in order to typically produce a viscosity of the final solution between about 2 and about 300 centipoise. Viscosity-increasing agents that are suitable for use in accordance with the present invention include, but are not limited to, polyvinylpyrrolidones, cellulose derivatives including, but not limited to, hydroxyethyl cellulose, carboxymethyl cellulose or its salts, hypromellose, carrageenan, guar gum, alginates, carbomers, polyethylene glycols, polyvinyl alcohol, and xanthan gum.

Another embodiment of the present invention is directed to topical formulations of a therapeutically effective amount of nefopam, nefopam metabolite, nefopam prodrug, isomers thereof or combinations of the foregoing and optionally an opioid analgesic and/or NSAID including occluded forms, such as matrix and reservoir patches, and unoccluded forms, such as gels, creams, lotions, ointments, and serums, as wells as topical foams and mousses.

Matrix patches in accordance with the present invention comprise the nefopam, nefopam metabolite, nefopam prodrug, isomers thereof or combinations of the foregoing and optionally opioid and/or NSAID homogeneously blended in a solid or semisolid polymer carrier together with other additives (e.g., permeation enhancers, plasticizers, viscosity reducing agent, and the like). The general structure and fabrication of matrix patches are well known in the art. In a preferred embodiment, the matrix patch comprises an occlusive backing that is impermeable to the nefopam, nefopam metabolite, nefopam prodrug, isomers thereof or combinations of the foregoing and defines the face or top surface of the patch and a solid or semisolid matrix layer comprised of a homogeneous blend of the nefopam, nefopam metabolite, nefopam prodrug, isomers thereof or combinations of the foregoing, a polymeric carrier, and one or more skin permeation enhancers.

The polymeric carrier may be adhesive or nonadhesive. When it is a pressure sensitive adhesive the basal surface of the matrix layer may be used to affix the patch to the skin. When it is not, other means such as an underlying adhesive layer, a peripheral adhesive layer, an adhesive overlay, or straps may be used to affix the patch to the skin.

Examples, without limitation, of specific polymers that may be used as the carrier are polyacrylates, polymethacrylates, natural and synthetic rubbers, silicone rubbers and elastomers, polyolefins, vinyl copolymers, urethanes, nylons, polyesters, polyethers, and the like.

The skin permeation enhancer(s) that are included in the matrix enhance the level of skin flux of nefopam, nefopam metabolite, nefopam prodrug, isomers thereof or combinations of the foregoing. Examples of permeation enhancers that may be used in compositions of the present invention include, but are not limited to, fatty acids, fatty acid esters, fatty alcohols, fatty acid esters of lactic acid or glycolic acid, glycerol tri-, di- and monoesters, triacetin, short chain alcohols, amine oxides and mixtures thereof. Particular examples of permeation enhancers include oleyl alcohol, lauryl alcohol, isopropyl myristate, oleyl oleate, levulinic acid, ethanol, glycerol monooleate, methyl laurate, sorbitain monooleate, triacetin, aloe vera oil, benzothonium chloride, cetyl dimethylamine oxide, cetyl alcohol, cetyl lactate, cocamidopropyl betaine, cocoamine oxide diethanolamine, dimethyloctylamine oxide, 2-dodecoxyethyldimethylamine oxide, dimethyl-decylamine oxide, dimethylhexadecylamine oxide, dimethyl-tetradecylamine oxide, dimethyl isosorbide, dipropylene glycol, ethyl hexyl lactate, glycolic acid, 3-dodecoxy-2-hydroxypropyldi(3-hydroxypropyl)amine oxide, lactic acid, lauramine oxide, lauryl betaine, lauryl lactate, lauryl laurate, isopropyl palmitate, macrogol 15 hydroxystearate (Solutol HS 15), menthol, menthyl lactate, myristyl alcohol, myristal lactate, octyldodecanol, octyl salicylate, oleamine oxide, oleic acid, oleyl betaine, oleyldi (2-hydroxyethyl) amine oxide, PEG 1000, pentadecalactone, propylene glycol, salicylic acid, stearyl alcohol, stearyl lactate, 3,6,9-trioxaheptadecyldiethylamine oxide, di(2-hydroxyethyl)-tetradecylamine oxide, triethanolamine triacetate and combinations thereof. Other permeation enhancers useful in the present invention may be found in U.S. Patent Application Publication No. 2007/0269379, which is incorporated in its entirety herein by reference. Preferred permeation enhancers include oleyl alcohol, lauryl alcohol, isopropyl myristate, oleyl oleate, levulinic acid, glycerol monooleate, methyl laurate, sorbitain monooleate, triacetin, cetyl alcohol, cetyl lactate, dimethyl isosorbide, dipropylene glycol, ethyl hexyl lactate, glycolic acid, lauramine oxide, lauryl betaine, lauryl lactate, lauryl laurate, isopropyl palmitate, myristyl alcohol, myristal lactate, octyl salicylate, oleamine oxide, oleic acid, oleyl betaine, salicylic acid, stearyl alcohol, stearyl lactate, triethanolamine triacetate and combinations thereof. The permeation enhancer will typically constitute about 1 to 20 wt % of the matrix, more typically 5 to 15 wt % of the matrix.

The patches of the invention may be manufactured by conventional techniques used in transdermal drug delivery device art. For instance, the nefopam, nefopam metabolite, nefopam prodrug, isomers thereof or combinations of the foregoing, carrier, and enhancer(s) may be mixed in the desired proportions to form a homogeneous mixture and cast or otherwise applied to a backing layer, by lamination to a release liner layer.

Reservoir patches in accordance with the present invention may comprise a gelled liquid solution or suspension containing nefopam, nefopam metabolite, nefopam prodrug, isomers thereof or combinations of the foregoing, optionally an opioid and/or NSAID and an enhancer within a carrier or be in the form of a fibrous body impregnated with the drug in the carrier. In addition to the reservoir, the device includes means for maintaining the reservoir in diffusional communication with the skin. Such means include a carrier which is also an adhesive, a separate basal adhesive layer underlying the reservoir, a peripheral ring of adhesive that is interconnected to the reservoir, an adhesive overlay for the reservoir, and straps. Preferably the means is either an adhesive carrier or a separate underlying adhesive layer.

In addition to the reservoir and affixation means, the patches may further include a backing that overlies the reservoir and protects the reservoir and/or prevents back-diffusion of nefopam, nefopam metabolite, nefopam prodrug, isomer thereof or combinations of the foregoing and enhancer from the reservoir, one or more structural layers to provide the device with appropriate mechanical properties, and/or a release liner layer that underlies the reservoir and which is removed prior to use and means for affixing the device to the skin.

The carrier or vehicle is permeable to nefopam, nefopam metabolite, nefopam prodrug, isomer thereof or combinations of the foregoing and the permeation enhancer. Preferably, the carrier is a fluid (e.g., liquid, gel, emulsion, suspension). It may be aqueous or nonaqueous. Examples of fluid carriers that may be used are alcohols such as ethanol, alcohol-water mixtures, and low molecular weight polymers such as polyethylene glycol. Ethanol is preferred and also provides permeation enhancement. In the case of ethanol, the carrier normally constitutes 20% to 70% by volume of the reservoir, more usually 40% to 60%, and preferably approximately 50%. Alternatively, the carrier may be a solid or semisolid matrix such as a pressure-sensitive adhesive.

The reservoir patches may contain a permeation enhancer as discussed above. The reservoir may also contain amounts of other materials such as gelling agents and anti-irritants. Glycerin is a preferred anti-irritant and may be present at about 5% to 50%, preferably about 20% to 30% by volume. The use of glycerin as an anti-irritant is described in U.S. Pat. No. 4,855,294.

The reservoir patches may be manufactured by conventional techniques used in the transdermal drug delivery device art. For instance, nefopam, nefopam metabolite, nefopam prodrug, isomers thereof or combinations of the foregoing, permeation enhancer and carrier may be mixed in the desired proportions to form a homogeneous mixture and cast or otherwise applied to a backing layer, followed by lamination to a release liner layer. If a separate basal adhesive layer is desired, it may be cast onto the release liner layer prior to such lamination.

For both matrix and reservoir patches, the diffusion coefficient of the nefopam, nefopam metabolite, nefopam prodrug, isomers thereof or combinations of the foregoing in the carrier will usually be between $10^{-4}$ and $10^{-12}$ cm$^2$/sec, more usually $10^{-5}$ and $10^{-8}$ cm$^2$/sec or between $1\times10^{-7}$ and $1\times10^{-10}$ cm$^2$/sec. Correspondingly, the solubility of the nefopam, nefopam metabolite, nefopam prodrug, isomers thereof or combinations of the foregoing in the carrier will usually be in the range of 1 to 500 mg/cm$^3$, preferably 1 to 200 mg/cm$^3$, and more preferably 10 to 100 mg/cm$^3$.

The patches will be typically designed to be worn for 1 to 14 days, more preferably 1 to 7 days, and most preferably 1-3 days. The thickness of the matrix layer may be 0.01 to 1 mm, more preferably 0.025 to 0.25 mm. The thickness of the reservoir will usually be about 0.01 to 5 mm, more usually 0.03 to 2 mm. The area of the patch in diffusional contact with the skin may be between 1 and 150 cm$^2$, more preferably 5 and 100 cm$^2$, and most preferably 10 and 75 cm$^2$. The required dosing may be supplied by a single device or by a plurality of devices applied to the skin.

A further embodiment of the present invention is directed to topical gels, creams, lotions, ointments, serums, foams, and mousses of nefopam, nefopam metabolite, nefopam prodrug, isomers thereof or combinations of the foregoing and optionally an opioid analgesic and/or NSAID (collectively "unoccluded topical dosage forms").

In addition to nefopam, nefopam metabolite, nefopam prodrug, isomers thereof or combinations of the foregoing, the unoccluded topical dosage forms may contain a penetration enhancer as discussed above. Depending upon the specific topical dosage form, i.e., serum, cream or foam, the topical dosage form of the present invention may also include further additives such as solvents, film forming/polymeric agents, viscosity increasing agents, emulsifiers, antioxidants, preservatives, pH adjusting agents, propellants and combinations of the foregoing. The unoccluded topical dosage forms may be uniform compositions, emulsions, such as oil-in-water or water-in-oil emlusions, or liposomal compositions.

The unoccluded topical dosage forms of the present invention may include any suitable solvent. Preferably, the solvent may include water and/or one or more organic compounds, e.g., esters, terpenes, alcohols, ketones, aldehydes, fatty acids, partially or fully esterified fatty acids, wherein the structures are cyclic, non-cyclic (e.g., alkyl), alicyclic (i.e., a bridged ring compound), or aromatic, as well as organic compounds having combinations of these functional groups. Specific examples of solvents that may be employed are water, methanol, ethanol, isopropyl alcohol, acetone, hexane, butyl alcohol, ethyl acetate, polyethylene glycol, propylene glycol, ethylene glycol, triethylene glycol, glycerin, 1,3-propane diol, 2-methyl-1,3-propane diol, glycerol ricinoleate, mineral oil, peanut oil, corn oil, cottonseed oil, sesame oil or a combination thereof. The solvent may be employed in any suitable amount. Typically, the solvent can be present in the unoccluded topical composition in about 1.0 wt % to about 95.0 wt % based upon the total weight of the unoccluded topical dosage form, preferably about 3.0 wt % to about 85 wt % based upon the total weight of the unoccluded topical composition and most preferably about 5.0 wt % to about 75 wt % of the total weight of the unoccluded topical composition.

The unoccluded topical dosage forms of the present invention also may optionally include a film-forming/polymeric agent. The film-forming/polymeric agent may enhance the adherence of the composition to the patient's skin and improve the composition's resistance to wash off or rub off. Film-forming/polymeric agents are preferably soluble or miscible with the nefopam, nefopam metabolite, nefopam prodrug, isomer thereof or combinations of the foregoing, solvent and/or penetration enhancer. The unoccluded topical dosage forms of the present invention typically comprises from about 0.001 wt % to about 25 wt %, preferably about 0.005 wt % to about 15 wt % and most preferably about 0.010 wt % to about 10 wt % based upon the total weight of the unoccluded topical composition of the film-forming/polymeric agent. Some examples of film-forming/polymeric agents that may be used in compositions of the present invention are polyalkenes, oleophilic copolymers of vinvylpyrrolidone, acrylic copolymers, polyethylene glycol derivative, polyolefins, polyurethanes and mixtures thereof.

Examples of polyalkenes that may be included in the topical dosage forms of the present invention are polyethylenes having a molecular weight ranging from about 300 to about 3000 (available as PERFORMALENE® from New Phase Technologies, Piscataway, N.J.); polyisobutylenes (available as VISTANEX™ from Exxon Chemical Company, Houston, Tex.); polyisobutenes (available as PRESPERSE™ from Sumitomo Corp.); polydecenes (SILKFLO™ available from Amoco); and hydrogenated polyisobutenes (PANALANE® available from Lipo Chemicals, Inc., Paterson, N.J.).

Oleophilic copolymers of vinylpyrollidone suitable for use in the topical dosage forms of the present invention may be copolymers of polyvinylpyrrolidone (PVP) and long chain alpha olefins, including, but not limited to, PVP/eicosene copolymers (GANEX® V-220 and V-220F), and tricontanyl PVP copolymers (GANEX®) available from Ashland, formerly International Specialty Products, Wayne, N.J.

Examples of acrylic copolymers that may be used in the topical dosage forms of the present invention include acrylic copolymers having long ($C_5$-$C_{30}$) alkyl chains to enhance their oleophilicity, such as acrylate/octylacrylamide copolymers (available as DERMACRYL® from Akzo Nobel). An example of a polyethylene glycol derivative that may be used as a film forming agent in compositions of the present invention is a polyethylene glycol derivative of Beeswax (ESTOL® E04BW-3752, E06BW-3753 or E03BW-3751 formerly available from Unichema, Wilmington, Del. and currently available from Croda under the trade name CITHROL®).

Examples of polyolefins that may be used as a film forming agent in compositions of the present invention are fatty acid ester/fatty acid anhydride grafted polyolefins wherein the esters and anhydrides are derived from $C_{12}$-$C_{22}$ fatty acid moieties, for example, $C_{30}$-$C_{38}$ olefin/isopropyl maleate/maleic anhydride copolymer (PERFORMA™ V 1608, available from New Phase Technologies, Piscataway, N.J.).

A preferred group of film forming/polymeric agents that may be used in the topical dosage forms of the present invention include polyurethanes derived from isophorone di-isocyanate such as those described in U.S. Pat. Nos. 5,051,260 and 6,613,866 and sold by Alzo International Inc. under the tradename POLYDERM®, polyisobutene/polybutene, hydrogentated polydecene and hydrogenated $C_6$-$C_{14}$ olefin polymers sold by ExxonMobil Chemical company under the tradename PURESYN®.

The film forming/polymeric agents may water-insoluble, oleophilic, water-resistant, or water-soluble.

The unoccluded topical dosage forms of the present invention may also contain viscosity enhancing agents that thicken, gel or harden the composition. An unoccluded topical dosage form in accordance with the present invention, such as a topical gel, typically comprises from about 0.001 wt % to about 50 wt % of the viscosity enhancing agent, preferably about 0.005 wt % to about 40 wt % and most preferably about 0.01 wt % to about 25 wt % based upon the total weight of the unoccluded topical composition. Exemplary viscosity enhancing agents include organic materials such as natural or synthetic waxes, $C_{12}$-$C_{60}$ alcohols, $C_{12}$-$C_{60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Additional viscosity enhancing agents include polyol polyesters, glyceryl esters, polyglyceryl esters and polysiloxanes that are a solid or semisolid at ambient temperature.

Specific examples of viscosity enhancing agents that may be included in the unoccluded topical dosage forms of the present invention include $C_{12}$-$C_{60}$ alcohols, preferably $C_{16}$-$C_{22}$ fatty alcohols, such as cetyl alcohol, stearyl alcohol, behenyl alcohol and mixtures thereof. Other suitable viscosity enhancing agents include $C_{12}$-$C_{60}$ acids, preferably $C_{16}$-$C_{22}$ fatty acids, such as palmitic acid, stearic acid, behenic acid, oleic acid, linoleic acid, myristic acid, ricinoleic acid, eurcic acid, lauric acid, isostearic acid and mixtures thereof. Further suitable viscosity enhancing agents that may be used herein are alpha-hydroxy fatty acids, including 12-hydroxystearic acid, 12-hydroxylauric acid, 16-hydroxyhexadecanoic acid and mixtures thereof. Additional examples of suitable fatty acids are further described in Klofta et al., U.S. Pat. No. 7,449,613, Hofrichter, et al., U.S. Pat. No. 5,429,816 and Motley, U.S. Pat. No. 5,552,136, disclosure of each is incorporated in its entirety herein by reference.

Waxes are also suitable for use as viscosity enhancing agents in unoccluded topical dosage forms of the present invention. Suitable natural waxes include, but are not limited to, carnauba, ozokerite, beeswax, candelilla, paraffin, ceresin, esparto, ouricuri, rezowax and other known mined and mineral waxes. Suitable synthetic waxes include, but are not limited to, paraffin waxes and microcrystalline waxes.

Additional viscosity enhancing agents that may be used include polyhydroxy fatty acid esters, polyhydroxy fatty acid amides and mixtures thereof. Preferred esters and amides will have three or more free hydroxy groups on the polyhydroxy moiety and are typically nonionic in character. Because of the possible skin sensitivity of those using articles to which the unoccluded topical dosage form is applied, these esters and amides should also be relatively mild and non-irritating to the skin. Suitable polyhydroxy fatty acid esters and polyhydroxy fatty acid amides are disclosed in Roe et al., U.S. Pat. No. 5,643,588, the disclosure of which is incorporated in its entirety herein by reference.

Still further viscosity enhancing agents that may be included in the unoccluded topical dosage forms of the present invention are gelling agents. Gelling agents are materials that can swell or expand when in contact with water. Examples of gelling agents that may be used in the present invention include swellable polymers, also known as osmopolymers or hydrogels as previously described. The swellable polymer can be non-cross-linked or lightly-cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include polyhydroalkylcellulose having a molecular weight greater than 50,000, such as hydroxyl propylmethylcellulose (METHOCEL® K 100M available from Dow Chemical); poly(hydroxyalkylmethacrylate) having a molecular weight of from 5,000 to 5,000,000; poly(vinylpyrrolidone) having a molecular weight of from 100,000 to 3,000,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams and the like.

Other gelling agents useful in the unoccluded topical dosage forms of the present invention include pectin having a molecular weight ranging from 30,000 to 300,000; polysaccharides such as agar, acacia, karaya, tragacanth, algins and guar; CARBOPOL®, an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOOD-RITE® polyacrylic acid having a molecular weight of 80,000 to 200,000; POLYOX® polyethylene oxide polymers having a molecular weight of 100,000 to 7,000,000; starch graft copolymers; AQUA-KEEP® acrylate polymers with water absorbability of about 400 times its original weight; diesters of polyglucan; a mixture of cross-linked polyvinyl alcohol and poly(N-vinyl-2-pyrrolidone); poly (ethylene glycol) having a molecular weight of 4,000 to 100,000. Representative polymers possessing gelling properties are described in U.S. Pat. Nos. 6,419,954, 4,915,949, 4,327,725, 4,207,893 and in *Handbook of Common Polymers*, by Scott and Roff, published by Cleveland Rubber Company, Cleveland, Ohio.

Examples of inorganic viscosity enhancing agents that may be included in the unoccluded topical dosage forms of the present invention include treated and untreated fumed silicas such as those available from Cabot Corp., Tuscola, Ill. under the trade designations CAB-O-SIL® M5 and MS-55. Exemplary surface-treated fumed silicas are also available from Cabot Corp., Tuscola, Ill. under the trade designations TS-720 and TS-610.

Suitable clays such as hectorite and smectite may also be used as viscosity enhancing agents in unoccluded topical dosage forms of the present invention.

Hydrogenated vegetable oils such as cocoa butter, shea butter and mixtures thereof may also be used as viscosity enhancing agents in unoccluded topical dosage forms of the present invention.

Suitable petroleum-based emollients may also be used as viscosity enhancing agents in unoccluded topical dosage forms of the present invention. Examples of suitable petroleum-based emollients that may be used include petrolatums, i.e., hydrocarbons or mixtures of hydrocarbons; particularly preferred are hydrocarbons having chain lengths of from $C_{10}$ to $C_{100}$. Petroleum-based emollients within this chain length range include mineral oil and petrolatum. Mineral oil usually refers to less viscous mixtures of hydrocarbons having from 10 to 30 carbon atoms, though the hydrocarbon molecular weight distribution may vary. Since the lower molecular weight hydrocarbons can cause irritation in some individuals, mineral oils having a small percentage of lower molecular weight hydrocarbons are preferred. Petrolatum usually refers to more viscous mixtures of hydrocarbons of higher molecular weight hydrocarbons. Petrolatum and mineral oil are preferred skin conditioning agents for compositions of the present invention due to their ability to protect the skin from harmful or irritating stimuli. Petrolatum is particularly preferred because of its good barrier properties.

The unoccluded topical dosage forms of the present invention may also contain humectants. Unoccluded topical dosage forms in accordance with the present invention typically comprises from about 0.001 wt % to about 30 wt % of a humectant, preferably about 0.005 wt % to about 20 wt % and most preferably about 0.01 wt % to about 10 wt % based upon the total weight of the unoccluded topical composition. Examples of compounds that may be used as humectants in compositions of the present invention are esters of polyhydroxy alcohols. This type of ester may include glyceryl esters including glycerides and derivatized glycerides, polyglyceryl esters, and glycolic esters. Glyceryl esters are derived from glycerin, its derivatives and one or more carboxylic acid moieties. Non-limiting examples include various $C_1$-$C_{30}$ mono-, di- or tri-esters of glycerin and derivatives thereof, such as mono-, di-, tri-glycerides, acetoglycerides, and ethoxylated glycerides. Exemplary glyceryl esters include glyceryl behenate, glyceryl oleate, glyceryl stearate, glyceryl palmitate, glyceryl distearate, glyceryl dipalmitate and the like. Polyglyceryl esters having $C_{12}$-$C_{22}$ acid moieties are also suitable for use herein. Non-limiting examples include polyglyceryl-4 isostearate, polyglyceryl-3 oleate, diglyceryl monooleate, tetraglyceryl monooleate and the like. Glycolic esters are derived from $C_2$-$C_6$ glycols, including ethylene glycol, propylene glycol, butylene glycol, hexylene glycol and derivatives thereof, and one or more carboxylic acid moieties having $C_1$-$C_{30}$ chains. Specific examples of glycolic esters include polyethylene glycols (PEGs), such as PEG-2, PEG-3, PEG-30 and PEG-50, and polypropylene glycols (PPGs), such as PPG-9, PPG-12, PPG-15, PPG-17, PPG-20, PPG-26, PPG-30 and PPG-34.

The unoccluded topical dosage forms of the present invention may also contain emulsifiers or dispersing agents such as anionic, cationic and nonionic surfactants. Unoccluded topical dosage forms in accordance with the present invention typically comprises from about 0.001 wt % to about 15 wt % of an emulsifier or dispersing agent, preferably about 0.005 wt % to about 10 wt % and most preferably about 0.01 wt % to about 5 wt % based upon the total weight of the unoccluded topical composition. Nonionic surfactants are preferred because of their low level of irritation to skin. Typical nonionic surfactants are monoglycerides such as glyceryl monostearate and the like; sorbitan aliphatic esters such as sorbitan monolaurate and the like; sucrose aliphatic esters; polyoxyethylene aliphatic esters such as polyoxyethylene stearate; and polyoxyethylene higher alcohol ethers such as polyoxyethylene cetyl ether, polyoxyethylene oleyl ether, polyoxyethylene fatty ethers and the like.

The unoccluded topical dosage forms of the present invention may also contain an antioxidant to minimize or prevent the oxidation process and enhance the shelf life of the composition. Unoccluded topical dosage forms in accordance with the present invention typically comprises from about 0.001 wt % to about 25 wt % of an anti-oxidant, preferably about 0.005 wt % to about 15 wt % and most preferably about 0.01 wt % to about 10 wt % based upon the total weight of the unoccluded topical composition. Antioxidants useful herein should preferably be mild and non-irritating. Antioxidants from natural sources are preferred, such as Vitamin E and its derivatives, including tocopherol, tocopherol acetate, mixed tocopherols (available as COVI-OX® T-50 or T-70 from Henkel Corp, Ambler, Pa.), and the like or butylated hydroxytoluene, butylated hydroxyanisole, sodium pyrosulfite, acetone sodium bisulfate and the like. Some of these antioxidants are also useful as skin antioxidants, which minimizes the wrinkles and dullness of the skin and provides a more youthful looking and firmer textured skin.

The unoccluded topical dosage forms of the present invention may also contain a preservative to prevent bacterial growth and odors thereof, particularly in compositions having a relatively high water content. Unoccluded topical dosage forms in accordance with the present invention typically comprise from about 0.001 wt % to about 10 wt % of a preservative, preferably about 0.005 wt % to about 5 wt % and most preferably about 0.01 wt % to about 2.5 wt % based upon the total weight of the unoccluded topical composition. Suitable preservatives include propyl paraben, methyl paraben, benzyl alcohol, benzalkonium chloride, tribasic calcium phosphate, phenoxyethanol, or acids such as citric, tartaric, maleic, lactic, malic, benzoic, salicylic and the like.

The unoccluded topical dosage forms of the present invention may include an acid or base to adjust the pH of the composition to the desired or optimal range. Examples of compounds typically used to adjust the pH of topical compositions include oleic acid, hydrochloric acid, citric acid, lactic acid, tartaric acid, glacial acetic acid, sodium hydroxide or the like. Depending upon the form in which the unoccluded topical dosage form is applied, i.e., gel, serum or cream, and the location, the desired final pH value of the composition may vary, however, it is generally preferred that the pH of the composition range from a pH of about 5.0 to about 8.5, preferably about 6 to about 8.0, and most preferably about 6.5 to about 7.5.

In order to increase the stability of the unoccluded topical dosage forms of the present invention, a chelating agent may be added. The chelating agents may include ethylenediaminetetraacetic acid (EDTA) and its derivatives, thioglycolic acid, thiolactic acid, thioglycerol and the like.

A fragrance may also be added to unoccluded topical dosage forms of the present invention if desired.

If the unoccluded topical dosage form of the present invention is an aerosol, foam or mouse, the composition will require a propellant for dispensing the composition from the container. The propellant may be any type of propellant commonly used in the cosmetic/pharmaceutical industry such as nitrogen, carbon dioxide, dimethyl ether, hydrocarbons, i.e., methane, ethane, propane, butanes and pentanes, halogenated hydrocarbons, i.e., $CH_2ClF$, $CClF_2CHClF$, $CF_3CHClF$, $CHF_2CClF_2$, $CHClFCHF_2$, $CF_3CH_2Cl$, $CClF_2CH_3$, $CHF_2CHF_2$, $CF_3CH_2F$ (HFC 134a), $CHF_2CH_3$ (HFC 152a), $CF_3CHFCF_3$ (HFC 227), $CF_3CF_3$ and $CF_3CF_2CF_3$. Some of the more commonly used hydrocarbon propellants are A-46 (15.2% propane/84.8% isobutene); and NP-46 (25.9% propane/74.1% n-butane), NIP-46 (21.9% propane/31.3% isobutene/46.8% n-butane). The amount of propellant will depend on the type of container for the composition of the present invention, the amount of the composition in the container, the amount of composition to be dispensed per actuation and the form in which the composition will be dispensed, i.e., mist or foam. The optimization of the propellant and container are within the ability of the skilled artisan and examples can be found in Wai-Chiu So et al., U.S. Pat. No. 6,946,120 and Remington, Science and Practice of Pharmacy, $21^{st}$ed., pp. 1000-1017 which are incorporated in their entirety herein by reference. The propellant is generally not included in the calculation of the weight percentages of the composition prepared in accordance with the present invention because it is merely part of the dispensing device and typically does not remain part of the composition once the composition is dispensed and applied to the patient's skin.

The aerosols, foams and mousses of the present invention will include a solvent, preferably water and/or a lower alcohol, i.e., $C_1$-$C_6$ alcohols such as methanol, ethanol, isopropanol or mixtures thereof. The aerosols, foams or mousses may also comprise a co-solvent selected from one or more of the group consisting of aromatic and polyhydric alcohols such as 1,3-butylene glycol, propylene glycol, polyethylene glycol 400, hexylene glycol and dipropylene glycol or glycerol. When the co-solvent is present, it may be present in amounts of approximately 10% by weight or less, preferably approximately 5% by weight or less based upon the total weight of the composition.

The emulsions of the present invention are either water-in-oil (W/O) emulsions or oil-in-water (O/W) emulsions, and may include, but are not limited to, cetyl alcohol, glyceryl monostearate, lanolin, polyalkylsiloxanes, and stearic acid. Water-soluble ointment bases suitable for use in the present invention may be prepared from polyethylene glycols of varying molecular weight. Emulsion formulations are generally formed from a dispersed phase (e.g., a pharmacologically active agent), a dispersion medium and an emulsifying agent. If desired, emulsion stabilizers can be included in the formulation as well. Emulsifying agents suitable for use in such formulations include, but are not limited to, TWEEN 60®, Span 80®, cetostearyl alcohol, myristyl alcohol, glyceryl monostearate and sodium lauryl sulfate.

W/O emulsions may be prepared by taking a mixture of the active agent(s) with oil phase ingredients, bacteriostats/preservatives and buffer salts which are dissolved or suspended therein and to which water has been added to form a water-in-oil emulsion. O/W emulsions are semisolid emulsions, micro-emulsions, or foam emulsion systems containing the active agent(s). Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

Another embodiment of the present invention is directed toward parenteral formulations wherein the nefopam, nefopam metabolite, nefopam prodrug, isomers thereof or combinations of the foregoing may be administered by intravenous, subcutaneous, intradermal, intramuscular, intraarticular or intrathecal injections. The parenteral formulation may comprise water for injection, nefopam, nefopam metabolite, nefopam prodrug, isomers thereof or combinations of the foregoing, and optionally an acid. The parenteral formulation may also comprise chemicals commonly employed in parenteral and/or IV fluids, such as sugars, amino acids, and/or electrolytes. The parenteral formulation may be packaged in vials or may be in the form of a dry powder that is packaged in a vial and that may be reconstituted with water.

In a preferred embodiment, the parenteral formulation provides for sustained release of the nefopam, nefopam metabolite, nefopam prodrug, isomers thereof or combinations of the foregoing by including multivesicular liposomes (MVL) that encapsulate and provide modulated and sustained release of the nefopam, nefopam metabolite, nefopam prodrug, isomer thereof or combinations of the foregoing. The MVL are made by the following process. A "water-in-oil" type emulsion containing a non-hydrohalic acid salt of nefopam, nefopam metabolite, nefopam prodrug, isomers thereof or combinations of the foregoing is formed from two immiscible phases, a lipid phase and a first aqueous phase.

The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholine, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamine.

Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

Many types of volatile organic solvents can be used in the present invention, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the anesthetic compositions of the present invention.

Optionally, but highly desirably, other components are included in the lipid phase. Among these are cholesterol or plant sterols.

The first aqueous phase includes nefopam, nefopam metabolite, nefopam prodrug, isomer thereof or combinations of the foregoing, at least one polyhydroxy carboxylic acid, and at least one di- or tri-protic mineral acid. In some embodiments of the invention, also included is hydrochloric acid. Hydrochloric acid is not an essential constituent, but rather is optional and desirable in some embodiments. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, the anesthetics of the invention are encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the anesthetic dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by spraying, rotary evaporation, or with the use of solvent selective membranes.

The present invention is also directed to methods of treating pain in a patient, preferably a mammal, and most preferably a human patient, or methods of reducing the dose of an opioid analgesic and/or NSAID by administering an oral solid formulation, topical formulation, or parenteral formulation of nefopam, nefopam metabolite, nefopam prodrug, isomers thereof or combinations of the foregoing as described above. Particular types of pain that may be suitably treated with the methods of the present invention include moderate to severe pain, perioperative pain, moderate to severe pain associated with skin graft surgery, and neuropathic pain, including post-herpetic neuralgia, diabetic neuropathic pain, central neuropathic pain, cancer pain, and phantom limb pain.

One method of the present invention is a method of treating moderate or severe pain or a method of reducing the dose of an opioid and/or NSAID by administering to a patient an enteric-coated formulation containing nefopam, nefopam metabolite, nefopam prodrug, isomer thereof or combinations of the foregoing, optionally an acid, such as citric acid, fumaric acid, or tartaric acid, and optionally an opioid and/or NSAID as described above.

Another method of the present invention is a method of treating moderate to severe perioperative pain or a method of reducing the dose of an opioid and/or NSAID by administering to a patient a parenteral formulation such as an IV formulation containing nefopam, nefopam metabolite, nefopam prodrug, isomer thereof or combinations of the foregoing, as described above, alone, or as part of a multi-modal PCA regimen including the administration of an opioid and/or NSAID.

A further method of the present invention is a method of treating moderate to severe perioperative pain or a method of reducing the dose of an opioid and/or NSAID by applying to a patient a foam or mousse formulation containing nefopam, nefopam metabolite, nefopam prodrug, isomers thereof or combinations of the foregoing, as described above, alone, or in combination with an opioid and/or NSAID.

An additional method of the present invention is a method of treating moderate to severe pain associated with skin graft surgery in patients suffering from skin trauma due to wounds, burns, fasciitis, and/or cancer or a method of reducing the dose of an opioid and/or NSAID by applying to the patient a foam or mousse formulation containing nefopam, nefopam metabolite, nefopam prodrug, isomer thereof or combinations of the foregoing, as described above, alone or in combination with an opioid and/or NSAID. In one embodiment of this method, the nefopam, nefopam metabolite, nefopam prodrug, isomers thereof or combinations of the foregoing is administered as an unoccluded topical composition, preferably in the form of a foam or mouse, to the trauma area, e.g., skin graft wound or burn region and the opioid and/or NSAID is administered orally.

A still further method of the present invention is a method of treating moderate to severe neuropathic pain, including post-herpetic neuralgia, diabetic neuropathic pain, and central neuropathic pain, or a method of reducing the dose of an opioid and/or NSAID by administering to a patient a transdermal or oral formulation containing nefopam, nefopam metabolite, nefopam prodrug, isomer thereof or combinations of the foregoing, as described above.

The methods of reducing the dose of an opioid analgesic and/or NSAID described above are accomplished by administering the opioid and/or NSAID as a component of the nefopam, nefopam metabolite, nefopam prodrug, isomers thereof or combinations of the foregoing formulations described herein or by administering the opioid and/or NSAID separately, but in combination with the nefopam, nefopam metabolite, nefopam prodrug, isomers thereof or combinations of the foregoing formulations described herein. The analgesic properties of nefopam, nefopam metabolite, nefopam prodrug, isomers thereof or combinations of the foregoing provide supplemental pain relief thereby allowing the dose of the opioid and/or NSAID to be reduced. As discussed above, reducing the dose of opioids is important for preventing dependence, addiction, and/or death from accidental overdose. In an embodiment of the methods above, the dose of the opioid analgesic and/or NSAID may be reduced by about 5-95%, preferably about 20-75%, and most preferably about 50-70% of the normal dose.

It is envisioned that any feature or element that is positively identified in this description may also be specifically excluded as a feature or element of an embodiment of the present invention as defined in the claims.

The invention described herein may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:

1. A method of treating pain in a patient comprising administering to the patient a pharmaceutical tablet comprising a homogenous matrix that comprises nefopam, nefopam metabolite, nefopam prodrug, isomer thereof or combinations of the foregoing, a carboxylic acid, and a modified release material wherein the tablet further comprises an opioid analgesic, NSAID, or combination thereof wherein the dose of opioid analgesic, NSAID, or combination thereof is about 50-70% of a normal dose.

2. The method of claim 1 wherein the carboxylic acid is citric acid, fumaric acid, tartaric acid, or a combination thereof.

3. The method of claim 1 wherein the modified release material comprises a controlled release material selected from the group consisting of alkylcelluloses, acrylic and methacrylic acid polymers and copolymers, cellulose ethers, and combinations thereof.

4. The method of claim 1 wherein the modified release material comprises an enteric polymer selected from the group consisting of shellac, methacrylic acid copolymers, cellulose acetate phthalate, hydroxypropylmethylcellulose phthalate, hydroxypropylmethylcellulose acetate succinate, cellulose acetate trimellitate, polyvinyl acetate phthalate and combinations thereof.

5. An orally-disintegrating tablet comprising nefopam, nefopam metabolite, nefopam prodrug, isomers thereof or combinations of the foregoing and a carboxylic acid wherein the orally-disintegrating tablet further comprising an opioid analgesic, NSAID, or combination thereof and wherein the dose of the opioid analgesic, NSAID or combination thereof is about 50-70% of a normal dose.

6. The orally-disintegrating tablet of claim 5 wherein the carboxylic acid is citric acid, fumaric acid, tartaric acid, or a combination thereof.

7. A method of treating pain in a patient comprising administering the orally-disintegrating tablet of claim 5.

8. The method of claim 7 wherein the orally-disintegrating tablet is administered sublingually or buccally.

* * * * *